(12) United States Patent
Caligiuri et al.

(10) Patent No.: US 10,815,272 B2
(45) Date of Patent: *Oct. 27, 2020

(54) CD31 PEPTIDES

(71) Applicants: INSTITUT NATIONAL DE LA SANTE ET DE LA RECHERCHE MEDICALE (INSERM), Paris (FR); UNIVERSITE PARIS DIDEROT—PARIS 7, Paris (FR); UNIVERSITE PARIS 13—PARIS NORD, Villetaneuse (FR); ASSISTANCE PUBLIQUE—HOPITAUX DE PARIS, Paris (FR)

(72) Inventors: Giuseppina Caligiuri, Paris (FR); Antonino Nicoletti, Paris (FR)

(73) Assignees: INSTITUT NATIONAL DE LA SANTE ET DE LA RECHERCHE MEDICALE (INSERM), Paris (FR); UNIVERSITE PARIS DIDEROT—PARIS 7, Paris (FR); UNIVERSITE PARIS 13—PARIS NORD, Paris (FR); ASSISTANCE PUBLIQUE—HOPITAUX DE PARIS, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 14/408,789

(22) PCT Filed: Jun. 19, 2013

(86) PCT No.: PCT/EP2013/062806
§ 371 (c)(1),
(2) Date: Dec. 17, 2014

(87) PCT Pub. No.: WO2013/190014
PCT Pub. Date: Dec. 27, 2013

(65) Prior Publication Data
US 2015/0203536 A1    Jul. 23, 2015

(30) Foreign Application Priority Data
Jun. 19, 2012 (EP) ..................... 12305697

(51) Int. Cl.
C07K 7/06      (2006.01)
A61K 38/17     (2006.01)
C07K 14/705    (2006.01)
A61K 38/00     (2006.01)

(52) U.S. Cl.
CPC ............ *C07K 7/06* (2013.01); *A61K 38/1774* (2013.01); *C07K 14/70596* (2013.01); *A61K 38/00* (2013.01)

(58) Field of Classification Search
None
See application file for complete search history.

(56) References Cited

U.S. PATENT DOCUMENTS 6,087,331 A    7/2000  Newman et al.

FOREIGN PATENT DOCUMENTS

WO    2010/000741 A1    1/2010
WO    2013152919        10/2013

OTHER PUBLICATIONS

Innovagen (peptide solubility calculator, accessed Jul. 20, 2017).*
Dahlmans et al., "A Novel Modification of the Peptide Synthesis on Polymeric Resins", Peptides, Sep. 24-30, 1972, pp. 171-172, Amsterdam.
Zehnder et al., "Involvement of CD31 in lymphocyte-mediated immune responses: importance of the membrane-proximal immunoglobulin domain and identification of an inhibiting CD31 peptide", Blood, Mar. 1, 1995, pp. 1282-1288, vol. 85, No. 5, American Society of Hematology, U.S.
Chen et al., "Administration of a CD31-derived peptide delays the onset and significantly increases survival from lethal graft-versus-host disease", Blood, Feb. 15, 1997, pp. 1452-1459, vol. 89, No. 4, American Society of Hematology, U.S.
Shah et al., "Eptifibatide: The evidence for its role in the management of acute coronary syndromes", Core Evid. Jun. 15, 2010;4:49-65.
Caligiuri et al., "Reduced immunoregulatory CD31+ T cells in patients with atherosclerotic abdominal aortic aneurysm", Arterioscler Thromb Vasc Biol. Mar. 2006;26(3):618-23.
Caligiuri et al., "Reduced immunoregulatory CD31+ T cells in the blood of atherosclerotic mice with plaque thrombosis", Arterioscler Thromb Vasc Biol. Aug. 2005;25(8):1659-64.
International search report of application PCT/EP2013/062806.
Demeure et al., "CD31 (PECAM-1) is a differentiation antigen lost during human CD4 T-cell maturation into Th1 or Th2 effector cells", Immunology. May 1996; 88(1): 110-115.
Fornasa et al., "A CD31-derived peptide prevents angiotensin II-induced atherosclerosis progression and aneurysm formation", Cardiovasc Res. Apr. 1, 2012;94(1):30-7.
Fornasa et al., "TCR stimulation drives cleavage and shedding of the ITIM receptor CD31.", J Immunol. May 15, 2010;184(10):5485-92.
Newman and Newman, "Signal transduction pathways mediated by PECAM-1: new roles for an old molecule in platelet and vascular cell biology", Arterioscler Thromb Vasc Biol. Jun. 1, 2003;23(6):953-64.

(Continued)

Primary Examiner — James H Alstrum-Acevedo
Assistant Examiner — Tara L Martinez
(74) Attorney, Agent, or Firm — W&C WIP

(57) ABSTRACT

The present invention provides peptides corresponding to fragments of CD31 that inhibit platelet and leukocyte activation, and to their use in the treatment of thrombotic disease. These peptides find use as therapeutic agents in the treatment of inflammatory diseases and thrombotic diseases such as atherothrombosis, in particular when immobilised onto solid supports.

15 Claims, 7 Drawing Sheets

Specification includes a Sequence Listing.

(56) References Cited

OTHER PUBLICATIONS

Newton-Nash and Newman, "A new role for platelet-endothelial cell adhesion molecule-1 (CD31): inhibition of TCR-mediated signal transduction", J Immunol. Jul. 15, 1999;163(2):682-8.

Stockinger et al., "Phenotype of human T cells expressing CD31, a molecule of the immunoglobulin supergene family", Immunology. Jan. 1992;75(1):53-8.

Kalinowska and Losy, "PECAM-1, a key player in neuroinflammation", Eur J Neurol. Dec. 2006;13(12):1284-90.

Liao et al., "Transgenic mice expressing different levels of soluble platelet/endothelial cell adhesion molecule-IgG display distinct inflammatory phenotypes", J Immunol. Nov. 15, 1999;163(10):5640-8.

Liao et al., "Soluble domain 1 of platelet-endothelial cell adhesion molecule (PECAM) is sufficient to block transendothelial migration in vitro and in vivo", J Exp Med. Apr. 7, 1997;185(7)1349-57.

Sato et al., "Clinical significance of soluble CD31 in patients with systemic sclerosis (SSc): association with limited cutaneous SSc", J Rheumatol. Nov. 2001;28(11):2460-5.

Woodfin et al., "PECAM-1: a multi-functional molecule in inflammation and vascular biology", Arterioscler Thromb Vasc Biol. Dec. 2007;27(12):2514-23.

Reinke et al.,"Short-term sPECAM-Fc treatment ameliorates EAE while chronic use hastens onset of symptoms", J Neuroimmunol. May 2007;186(1-2):86-93.

Flego et al., "Altered CD31 expression and activity in helper T cells of acute coronary syndrome patients", Basic Res Cardiol. 2014;109(6):448.

* cited by examiner

FIG.1
Beginning

```
HUMAN  MQPRWAQGATMWLGVLLTLLLCSSLEGQENSFTINSVDMKSLPDWTVQNGKNLTLQCFAD  60
MOUSE  ------MLLALGLTLVLYASLQAEENSFTINSIHMESLPSWEVMNGQOLTLECLVD       50
BOVIN  MQLRWTQRGMMWLIGALLTLLLCSSLKGQENSFTINSIHMQILPHSTVQNGENLTLQCLVD  60
PIG    MRLRWTQGGNMWLGVLLTLQLCSSLEGQENSFTINSIHMEMLPGQEVHNGENLTLQCIVD  60

HUMAN  VSTTSHVKPQHQMLFYKDDVLFYNISSMKSTESYFIPEVRIYDSGTYKCTVIVNNKEKTT  120
MOUSE  ISTTSKSRSQHRVLFYKDDAMVYNVTSREHTESYVIPQARVFHSGKYKCTVMLNNKEKTT  110
BOVIN  VSTTSRVKPLHQVLFYKDDVLLHNVSSRRNTESYLIPHVRVCDSGRYKCNVILNNKEKTT  120
PIG    VSTTSSVKPQHQVLFYKDDVLFHNVSSTKNTESYFISEARVYNSGRYKCTVILNNKEKTT  120

HUMAN  AEYQLLVEGVPSPRVTLDKKEAIQGGIVRVNCSVPEEKAPIHFTIEKLELNEKMVKLRE   180
MOUSE  IEYEVKVHGVSKPKVTLDKKEVTEGGVVTVNCSLQEEKPPIFFKIEKLEVGTKFVKRRID  170
BOVIN  PEYEVWVKGVSDPRVTLDKKEVIEGGVVVVNCSVPEEKAPVHFTIEKFELNIRGAKKKRE  180
PIG    AEYKVVVEGVSNPRVTLDKKEVIEGGVVKVTCSVPEEKPPVHFIIEKFELNVRDVKQRRE  180

HUMAN  KNSRDQNFVILEFPVEEQDRVLSFRCQARIISGIHMQTSESTKSELVTVTESFSTPKFHI  240
MOUSE  KTS-NENFVLMEFPIEAQDHVLVFRCQAGILSGFKLQESEPIRSEYVTVQESFSTPKFEI  229
BOVIN  KTSQNQNFVTLEFTVEEQDRTIRFQCQAKIFSGSNVESSRPIQSDLVTVRESFSNPKFHI  240
PIG    KTANNQNSVTLEFTVEEQDRVILFSCQANVIFGTRVEISDSVRSDLVTVRESFSNPKFHI  240

HUMAN  SPTGMIMEGAQLHIKCTIQVTHLAQEFPEIIIQKDKAIVAHNRHGNKAVYSVMAMVEHSG  300
MOUSE  KPPGMIIEGDQLHIRCIVQVTHLVQEFTEIIIQKDKAIVATSKQSSEAVYSVMAMVEYSG  289
BOVIN  IPEGKVMEGDDLQVKCTVQVTHQAQSFPEIIIQKDREIVAHNSLSSEAVYSVMATTEHNG  300
PIG    SPKGVIIEGDQLLIKCTIQVTHQAQSFPEIIIQKDKEIVAHSRNGSEAVYSVMATVEHNS  300

HUMAN  NYTCKVESSRISKVSSIVVNITELFSKPELESSFTHLDQGERLNLSCSIPGAPP-ANFTI  359
MOUSE  HYTCKVESNRISKASSIMVNITELFPKPKLEFSSSRLDQGELLDLSCSVSGTPV-ANFTI  348
BOVIN  NYTCKVEASRISKVSSVVVNTELFSKPKLESSATHLDQGEDLNLLCSIPGAPP-ANFTI  359
PIG    NYTCKVEASRISKVSSIMVNITELFSRPKLKSSATRLDQGESLRIWCSIPGAPPEANFTI  360

HUMAN  QKEDTIVSQTQDFTKIASKSDSGTYICTAGIDKVVKKSNTVQIVVCEMLSQPRISYDAQF  419
MOUSE  QKEETVLSQYQNFSKIAEESDSGEYSCTAGIGKVVKRSGLVPIQVCEMLSKPSIFHDAKS  408
BOVIN  QKGGMTVSQTQNFTKRVSEWDSGLYTCVAGVGRVFKRSNTVQITVCEMLSKPSIFHDSRS  419
PIG    QKGGMMLQDQNLTKVASERDSGTYTCVAGIGKVVKRSNEVQIAVCEMLSKPSIFHDSGS  420
```

| | | |
|---|---|---|
| HUMAN | EVIKGQTIEVRCESISGTLPISYQLLKTSKVLENSTKNSNDPAVFKDNPTEDVEYQCVAD | 479 |
| MOUSE | EIIKGHAIGISCQSENGTAPITYHLMKAKSDFQTLEVTSNDPATFTDKPTRDMEYQCRAD | 468 |
| BOVIN | EVIKGQTIEVSCQSVNGTAPIFYQLSNTSKPVANQSVGSNKPAIFRVKPTKDVEYCCSAD | 479 |
| PIG   | EVIKGQTIEVSCQSINGTSPISYQLLKGSDLLASQNVSSNEPAVFKDNPTKDVEYQCIAD | 480 |
| HUMAN | NCHSHAKMLSEVLRVKVIAPVDEVQISILSSKVVESGEDIVLQCAVNEGSGPITYKFYRE | 539 |
| MOUSE | NCHSHPAVFSEILRVRVIAPVDEVVISILSSNEVQSGSEMVLRCSVKEGTSPITFQFYKE | 528 |
| BOVIN | NCHSHSKMFSEVLRVKVIAPVDEAQL-VVLKGEVEPGEPIVFYCSVNEGSFPITYKFYKE | 538 |
| PIG   | NCHSHAGMPSKVLRVKVIAPVEEVKLSILLSEEVESGQAIVLQCSVKEGSGPITYKFYKE | 540 |
| HUMAN | KEGKPFYQMTSNATQAFWTKQKASKEQEGEYYCTAFNRANHASSVPRSKILTVRVILAPW | 599 |
| MOUSE | KEDRPFHQAVVNDTQAFWHNKQASKKQEGQYYCTASNRASSMRTSPRSSTLAVRVFLAPW | 588 |
| BOVIN | KESKPFYQDTINATQIMWHKTTASKEYEGQYYCTASNRANLSKHVIQSNTLTVRVL-PL  | 597 |
| PIG   | KENKPFHQVTLNDTQAIWHKPKASKDQEGQYYCLASNRATPSKNFLQSNILAVRVYLAPW | 600 |
| HUMAN | KKGLIAVVIGVIIALLIIAAKCYFLRKAKAKQMPVEMSRPAVPLLNSNNEK-MSDPNME  | 658 |
| MOUSE | KKGLIAVVIGVVIGVIIATLIVAAKCYFLRKAKAKQKPVEMSRPAAPLLNSNSEK-ISEPSVE | 647 |
| BOVIN | EKGLIAVVIGVIITVTLVLGAKCYFLKKAKAKQMPVEMSRPAVPLLNSNNEKTLSDAGTE | 657 |
| PIG   | KKGLIAVVIAVIIAVLLLGARFYFLKKSKAKQMPVEMCRPAAPLLNSNNEKTLSDPNTE  | 660 |
| HUMAN | ANSHYGHNDDVRNHAMKPINDNKEPLNSDVQYTEVQVSSAESHKDLGKKD--TETVYSEV | 716 |
| MOUSE | ANSHYGYDDVSGNDAVKPINQNKDPQNMDVEYTEVEVSSLEPHQALGTRA--TETVYSEI | 705 |
| BOVIN | ADRHYGYNEDVGNHAMKPLNENKEPLTLDVEYTEVEVTSPEPHQGLGTKGTETETVYSEI | 717 |
| PIG   | ANRHYGYNEDVGNHAMKPLNENKEPLTLDVEYTEVEVTSPEPHRGLGTKG--TETVYSEI | 718 |
| HUMAN | RKAVPDAVESRYSRTEGSLDGT | 738 |
| MOUSE | RKVDPNLMENRYSRTEGSLNGT | 727 |
| BOVIN | RKADPDFVENRYSRTEGSLDGS | 739 |
| PIG   | RKADPDLVENRYSRTEGSLDGT | 740 |

FIG.1 End

SEQUENCE LISTING

```
<160> NUMBER OF SEQ ID NOS: 8

<210> SEQ ID NO 1
<211> LENGTH: 738
<212> TYPE: PRT
<213> ORGANISM: Homo sapiens
<220> FEATURE:
<221> NAME/KEY: SIGNAL
<222> LOCATION: (1)..(27)
<220> FEATURE:
<221> NAME/KEY: DOMAIN
<222> LOCATION: (28)..(601)
<223> OTHER INFORMATION: extracellular domain
<220> FEATURE:
<221> NAME/KEY: DOMAIN
<222> LOCATION: (34)..(121)
<223> OTHER INFORMATION: First Ig-like domain
<220> FEATURE:
<221> NAME/KEY: DOMAIN
<222> LOCATION: (145)..(233)
<223> OTHER INFORMATION: Second Ig-like domain
<220> FEATURE:
<221> NAME/KEY: DOMAIN
<222> LOCATION: (236)..(315)
<223> OTHER INFORMATION: Third Ig-like domain
<220> FEATURE:
<221> NAME/KEY: DOMAIN
<222> LOCATION: (328)..(401)
<223> OTHER INFORMATION: Fourth Ig-like domain
<220> FEATURE:
<221> NAME/KEY: DOMAIN
<222> LOCATION: (424)..(493)
<223> OTHER INFORMATION: Fifth Ig-like domain
<220> FEATURE:
<221> NAME/KEY: DOMAIN
<222> LOCATION: (499)..(591)
<223> OTHER INFORMATION: Sixth Ig-like domain
<220> FEATURE:
<221> NAME/KEY: DOMAIN
<222> LOCATION: (602)..(620)
<223> OTHER INFORMATION: transmembrane domain
<220> FEATURE:
<221> NAME/KEY: DOMAIN
<222> LOCATION: (621)..(738)
<223> OTHER INFORMATION: cytoplasmic

<400> SEQUENCE: 1

Met Gln Pro Arg Trp Ala Gln Gly Ala Thr Met Trp Leu Gly Val Leu
```

```
1               5                   10                  15
Leu Thr Leu Leu Leu Cys Ser Ser Leu Glu Gly Gln Glu Asn Ser Phe
                20                  25                  30

Thr Ile Asn Ser Val Asp Met Lys Ser Leu Pro Asp Trp Thr Val Gln
                35                  40                  45

Asn Gly Lys Asn Leu Thr Leu Gln Cys Phe Ala Asp Val Ser Thr Thr
        50                  55                  60

Ser His Val Lys Pro Gln His Gln Met Leu Phe Tyr Lys Asp Asp Val
65                  70                  75                  80

Leu Phe Tyr Asn Ile Ser Ser Met Lys Ser Thr Glu Ser Tyr Phe Ile
                85                  90                  95

Pro Glu Val Arg Ile Tyr Asp Ser Gly Thr Tyr Lys Cys Thr Val Ile
                100                 105                 110

Val Asn Asn Lys Glu Lys Thr Thr Ala Glu Tyr Gln Leu Leu Val Glu
                115                 120                 125

Gly Val Pro Ser Pro Arg Val Thr Leu Asp Lys Lys Glu Ala Ile Gln
130                 135                 140

Gly Gly Ile Val Arg Val Asn Cys Ser Val Pro Glu Glu Lys Ala Pro
145                 150                 155                 160

Ile His Phe Thr Ile Glu Lys Leu Glu Leu Asn Glu Lys Met Val Lys
                165                 170                 175

Leu Lys Arg Glu Lys Asn Ser Arg Asp Gln Asn Phe Val Ile Leu Glu
                180                 185                 190

Phe Pro Val Glu Glu Gln Asp Arg Val Leu Ser Phe Arg Cys Gln Ala
                195                 200                 205

Arg Ile Ile Ser Gly Ile His Met Gln Thr Ser Glu Ser Thr Lys Ser
210                 215                 220

Glu Leu Val Thr Val Thr Glu Ser Phe Ser Thr Pro Lys Phe His Ile
225                 230                 235                 240

Ser Pro Thr Gly Met Ile Met Glu Gly Ala Gln Leu His Ile Lys Cys
                245                 250                 255

Thr Ile Gln Val Thr His Leu Ala Gln Glu Phe Pro Glu Ile Ile Ile
                260                 265                 270

Gln Lys Asp Lys Ala Ile Val Ala His Asn Arg His Gly Asn Lys Ala
                275                 280                 285

Val Tyr Ser Val Met Ala Met Val Glu His Ser Gly Asn Tyr Thr Cys
                290                 295                 300

Lys Val Glu Ser Ser Arg Ile Ser Lys Val Ser Ser Ile Val Val Asn
305                 310                 315                 320

Ile Thr Glu Leu Phe Ser Lys Pro Glu Leu Glu Ser Ser Phe Thr His
                325                 330                 335

Leu Asp Gln Gly Glu Arg Leu Asn Leu Ser Cys Ser Ile Pro Gly Ala
                340                 345                 350

Pro Pro Ala Asn Phe Thr Ile Gln Lys Glu Asp Thr Ile Val Ser Gln
                355                 360                 365

Thr Gln Asp Phe Thr Lys Ile Ala Ser Lys Ser Asp Ser Gly Thr Tyr
                370                 375                 380

Ile Cys Thr Ala Gly Ile Asp Lys Val Val Lys Lys Ser Asn Thr Val
385                 390                 395                 400

Gln Ile Val Val Cys Glu Met Leu Ser Gln Pro Arg Ile Ser Tyr Asp
                405                 410                 415

Ala Gln Phe Glu Val Ile Lys Gly Gln Thr Ile Glu Val Arg Cys Glu
                420                 425                 430
```

Ser Ile Ser Gly Thr Leu Pro Ile Ser Tyr Gln Leu Leu Lys Thr Ser
            435                 440                 445

Lys Val Leu Glu Asn Ser Thr Lys Asn Ser Asn Asp Pro Ala Val Phe
        450                 455                 460

Lys Asp Asn Pro Thr Glu Asp Val Glu Tyr Gln Cys Val Ala Asp Asn
465                 470                 475                 480

Cys His Ser His Ala Lys Met Leu Ser Glu Val Leu Arg Val Lys Val
            485                 490                 495

Ile Ala Pro Val Asp Glu Val Gln Ile Ser Ile Leu Ser Ser Lys Val
            500                 505                 510

Val Glu Ser Gly Glu Asp Ile Val Leu Gln Cys Ala Val Asn Glu Gly
            515                 520                 525

Ser Gly Pro Ile Thr Tyr Lys Phe Tyr Arg Glu Lys Glu Gly Lys Pro
            530                 535                 540

Phe Tyr Gln Met Thr Ser Asn Ala Thr Gln Ala Phe Trp Thr Lys Gln
545                 550                 555                 560

Lys Ala Ser Lys Glu Gln Glu Gly Glu Tyr Tyr Cys Thr Ala Phe Asn
            565                 570                 575

Arg Ala Asn His Ala Ser Ser Val Pro Arg Ser Lys Ile Leu Thr Val
            580                 585                 590

Arg Val Ile Leu Ala Pro Trp Lys Lys Gly Leu Ile Ala Val Val Ile
            595                 600                 605

Ile Gly Val Ile Ile Ala Leu Leu Ile Ile Ala Ala Lys Cys Tyr Phe
            610                 615                 620

Leu Arg Lys Ala Lys Ala Lys Gln Met Pro Val Glu Met Ser Arg Pro
625                 630                 635                 640

Ala Val Pro Leu Leu Asn Ser Asn Asn Glu Lys Met Ser Asp Pro Asn
                    645                 650                 655

Met Glu Ala Asn Ser His Tyr Gly His Asn Asp Asp Val Arg Asn His
            660                 665                 670

Ala Met Lys Pro Ile Asn Asp Asn Lys Glu Pro Leu Asn Ser Asp Val
            675                 680                 685

Gln Tyr Thr Glu Val Gln Val Ser Ser Ala Glu Ser His Lys Asp Leu
            690                 695                 700

Gly Lys Lys Asp Thr Glu Thr Val Tyr Ser Glu Val Arg Lys Ala Val
705                 710                 715                 720

Pro Asp Ala Val Glu Ser Arg Tyr Ser Arg Thr Glu Gly Ser Leu Asp
            725                 730                 735

Gly Thr

<210> SEQ ID NO 2
<211> LENGTH: 727
<212> TYPE: PRT
<213> ORGANISM: Mus musculus

<400> SEQUENCE: 2

Met Leu Leu Ala Leu Gly Leu Thr Leu Val Leu Tyr Ala Ser Leu Gln
1               5                   10                  15

Ala Glu Glu Asn Ser Phe Thr Ile Asn Ser Ile His Met Glu Ser Leu
            20                  25                  30

Pro Ser Trp Glu Val Met Asn Gly Gln Gln Leu Thr Leu Glu Cys Leu
        35                  40                  45

Val Asp Ile Ser Thr Thr Ser Lys Ser Arg Ser Gln His Arg Val Leu
    50                  55                  60

```
Phe Tyr Lys Asp Asp Ala Met Val Tyr Asn Val Thr Ser Arg Glu His
 65                  70                  75                  80

Thr Glu Ser Tyr Val Ile Pro Gln Ala Arg Val Phe His Ser Gly Lys
             85                  90                  95

Tyr Lys Cys Thr Val Met Leu Asn Asn Lys Glu Lys Thr Thr Ile Glu
            100                 105                 110

Tyr Glu Val Lys Val His Gly Val Ser Lys Pro Lys Val Thr Leu Asp
            115                 120                 125

Lys Lys Glu Val Thr Glu Gly Val Val Thr Val Asn Cys Ser Leu
130                 135                 140

Gln Glu Glu Lys Pro Pro Ile Phe Phe Lys Ile Glu Lys Leu Glu Val
145                 150                 155                 160

Gly Thr Lys Phe Val Lys Arg Arg Ile Asp Lys Thr Ser Asn Glu Asn
            165                 170                 175

Phe Val Leu Met Glu Phe Pro Ile Glu Ala Gln Asp His Val Leu Val
            180                 185                 190

Phe Arg Cys Gln Ala Gly Ile Leu Ser Gly Phe Lys Leu Gln Glu Ser
            195                 200                 205

Glu Pro Ile Arg Ser Glu Tyr Val Thr Val Gln Glu Ser Phe Ser Thr
210                 215                 220

Pro Lys Phe Glu Ile Lys Pro Pro Gly Met Ile Ile Glu Gly Asp Gln
225                 230                 235                 240

Leu His Ile Arg Cys Ile Val Gln Val Thr His Leu Val Gln Glu Phe
            245                 250                 255

Thr Glu Ile Ile Ile Gln Lys Asp Lys Ala Ile Val Ala Thr Ser Lys
            260                 265                 270

Gln Ser Ser Glu Ala Val Tyr Ser Val Met Ala Met Val Glu Tyr Ser
275                 280                 285

Gly His Tyr Thr Cys Lys Val Glu Ser Asn Arg Ile Ser Lys Ala Ser
            290                 295                 300

Ser Ile Met Val Asn Ile Thr Glu Leu Phe Pro Lys Pro Lys Leu Glu
305                 310                 315                 320

Phe Ser Ser Ser Arg Leu Asp Gln Gly Glu Leu Leu Asp Leu Ser Cys
                325                 330                 335

Ser Val Ser Gly Thr Pro Val Ala Asn Phe Thr Ile Gln Lys Glu Glu
            340                 345                 350

Thr Val Leu Ser Gln Tyr Gln Asn Phe Ser Lys Ile Ala Glu Glu Ser
            355                 360                 365

Asp Ser Gly Glu Tyr Ser Cys Thr Ala Gly Ile Gly Lys Val Val Lys
            370                 375                 380

Arg Ser Gly Leu Val Pro Ile Gln Val Cys Glu Met Leu Ser Lys Pro
385                 390                 395                 400

Ser Ile Phe His Asp Ala Lys Ser Glu Ile Ile Lys Gly His Ala Ile
            405                 410                 415

Gly Ile Ser Cys Gln Ser Glu Asn Gly Thr Ala Pro Ile Thr Tyr His
            420                 425                 430

Leu Met Lys Ala Lys Ser Asp Phe Gln Thr Leu Glu Val Thr Ser Asn
            435                 440                 445

Asp Pro Ala Thr Phe Thr Asp Lys Pro Thr Arg Asp Met Glu Tyr Gln
            450                 455                 460

Cys Arg Ala Asp Asn Cys His Ser His Pro Ala Val Phe Ser Glu Ile
465                 470                 475                 480
```

```
Leu Arg Val Arg Val Ile Ala Pro Val Asp Glu Val Val Ile Ser Ile
                485                 490                 495

Leu Ser Ser Asn Glu Val Gln Ser Gly Ser Glu Met Val Leu Arg Cys
            500                 505                 510

Ser Val Lys Glu Gly Thr Ser Pro Ile Thr Phe Gln Phe Tyr Lys Glu
        515                 520                 525

Lys Glu Asp Arg Pro Phe His Gln Ala Val Val Asn Asp Thr Gln Ala
    530                 535                 540

Phe Trp His Asn Lys Gln Ala Ser Lys Lys Gln Glu Gly Gln Tyr Tyr
545                 550                 555                 560

Cys Thr Ala Ser Asn Arg Ala Ser Ser Met Arg Thr Ser Pro Arg Ser
                565                 570                 575

Ser Thr Leu Ala Val Arg Val Phe Leu Ala Pro Trp Lys Lys Gly Leu
            580                 585                 590

Ile Ala Val Val Ile Gly Val Val Ile Ala Thr Leu Ile Val Ala
        595                 600                 605

Ala Lys Cys Tyr Phe Leu Arg Lys Ala Lys Ala Lys Gln Lys Pro Val
    610                 615                 620

Glu Met Ser Arg Pro Ala Ala Pro Leu Leu Asn Ser Asn Ser Glu Lys
625                 630                 635                 640

Ile Ser Glu Pro Ser Val Glu Ala Asn Ser His Tyr Gly Tyr Asp Asp
                645                 650                 655

Val Ser Gly Asn Asp Ala Val Lys Pro Ile Asn Gln Asn Lys Asp Pro
            660                 665                 670

Gln Asn Met Asp Val Glu Tyr Thr Glu Val Glu Val Ser Ser Leu Glu
        675                 680                 685

Pro His Gln Ala Leu Gly Thr Arg Ala Thr Thr Val Tyr Ser Glu
    690                 695                 700

Ile Arg Lys Val Asp Pro Asn Leu Met Glu Asn Arg Tyr Ser Arg Thr
705                 710                 715                 720

Glu Gly Ser Leu Asn Gly Thr
                725

<210> SEQ ID NO 3
<211> LENGTH: 739
<212> TYPE: PRT
<213> ORGANISM: Bos taurus

<400> SEQUENCE: 3

Met Gln Leu Arg Trp Thr Gln Arg Gly Met Met Trp Leu Gly Ala Leu
1               5                   10                  15

Leu Thr Leu Leu Leu Cys Ser Ser Leu Lys Gly Gln Glu Asn Ser Phe
            20                  25                  30

Thr Ile Asn Ser Ile His Met Gln Ile Leu Pro His Ser Thr Val Gln
        35                  40                  45

Asn Gly Glu Asn Leu Thr Leu Gln Cys Leu Val Asp Val Ser Thr Thr
    50                  55                  60

Ser Arg Val Lys Pro Leu His Gln Val Leu Phe Tyr Lys Asp Asp Val
65                  70                  75                  80

Leu Leu His Asn Val Ser Ser Arg Arg Asn Thr Glu Ser Tyr Leu Ile
                85                  90                  95

Pro His Val Arg Val Cys Asp Ser Gly Arg Tyr Lys Cys Asn Val Ile
            100                 105                 110

Leu Asn Asn Lys Glu Lys Thr Thr Pro Glu Tyr Glu Val Trp Val Lys
        115                 120                 125
```

```
Gly Val Ser Asp Pro Arg Val Thr Leu Asp Lys Lys Glu Val Ile Glu
130                 135                 140

Gly Gly Val Val Val Asn Cys Ser Val Pro Glu Glu Lys Ala Pro
145                 150                 155                 160

Val His Phe Thr Ile Glu Lys Phe Glu Leu Asn Ile Arg Gly Ala Lys
                165                 170                 175

Lys Lys Arg Glu Lys Thr Ser Gln Asn Gln Asn Phe Val Thr Leu Glu
            180                 185                 190

Phe Thr Val Glu Glu Gln Asp Arg Thr Ile Arg Phe Gln Cys Gln Ala
        195                 200                 205

Lys Ile Phe Ser Gly Ser Asn Val Glu Ser Ser Arg Pro Ile Gln Ser
210                 215                 220

Asp Leu Val Thr Val Arg Glu Ser Phe Ser Asn Pro Lys Phe His Ile
225                 230                 235                 240

Ile Pro Glu Gly Lys Val Met Glu Gly Asp Asp Leu Gln Val Lys Cys
                245                 250                 255

Thr Val Gln Val Thr His Gln Ala Gln Ser Phe Pro Glu Ile Ile Ile
            260                 265                 270

Gln Lys Asp Arg Glu Ile Val Ala His Asn Ser Leu Ser Ser Glu Ala
        275                 280                 285

Val Tyr Ser Val Met Ala Thr Thr Glu His Asn Gly Asn Tyr Thr Cys
290                 295                 300

Lys Val Glu Ala Ser Arg Ile Ser Lys Val Ser Ser Val Val Val Asn
305                 310                 315                 320

Val Thr Glu Leu Phe Ser Lys Pro Lys Leu Glu Ser Ser Ala Thr His
                325                 330                 335

Leu Asp Gln Gly Glu Asp Leu Asn Leu Leu Cys Ser Ile Pro Gly Ala
            340                 345                 350

Pro Pro Ala Asn Phe Thr Ile Gln Lys Gly Gly Met Thr Val Ser Gln
        355                 360                 365

Thr Gln Asn Phe Thr Lys Arg Val Ser Glu Trp Asp Ser Gly Leu Tyr
370                 375                 380

Thr Cys Val Ala Gly Val Gly Arg Val Phe Lys Arg Ser Asn Thr Val
385                 390                 395                 400

Gln Ile Thr Val Cys Glu Met Leu Ser Lys Pro Ser Ile Phe His Asp
                405                 410                 415

Ser Arg Ser Glu Val Ile Lys Gly Gln Thr Ile Glu Val Ser Cys Gln
            420                 425                 430

Ser Val Asn Gly Thr Ala Pro Ile Phe Tyr Gln Leu Ser Asn Thr Ser
        435                 440                 445

Lys Pro Val Ala Asn Gln Ser Val Gly Ser Asn Lys Pro Ala Ile Phe
450                 455                 460

Arg Val Lys Pro Thr Lys Asp Val Glu Tyr Cys Cys Ser Ala Asp Asn
465                 470                 475                 480

Cys His Ser His Ser Lys Met Phe Ser Glu Val Leu Arg Val Lys Val
                485                 490                 495

Ile Ala Pro Val Asp Glu Ala Gln Leu Val Val Leu Lys Gly Glu Val
            500                 505                 510

Glu Pro Gly Glu Pro Ile Val Phe Tyr Cys Ser Val Asn Glu Gly Ser
        515                 520                 525

Phe Pro Ile Thr Tyr Lys Phe Tyr Lys Glu Lys Glu Ser Lys Pro Phe
530                 535                 540
```

```
Tyr Gln Asp Thr Ile Asn Ala Thr Gln Ile Met Trp His Lys Thr Thr
545                 550                 555                 560

Ala Ser Lys Glu Tyr Glu Gly Gln Tyr Tyr Cys Thr Ala Ser Asn Arg
            565                 570                 575

Ala Asn Leu Ser Lys His Val Ile Gln Ser Asn Thr Leu Thr Val Arg
            580                 585                 590

Val Tyr Leu Pro Leu Glu Lys Gly Leu Ile Ala Val Val Ile Gly
            595                 600                 605

Val Ile Ile Val Thr Leu Val Leu Gly Ala Lys Cys Tyr Phe Leu Lys
610                 615                 620

Lys Ala Lys Ala Lys Gln Met Pro Val Glu Met Ser Arg Pro Ala Val
625                 630                 635                 640

Pro Leu Leu Asn Ser Asn Asn Glu Lys Thr Leu Ser Asp Ala Gly Thr
            645                 650                 655

Glu Ala Asp Arg His Tyr Gly Tyr Asn Glu Asp Val Gly Asn His Ala
            660                 665                 670

Met Lys Pro Leu Asn Glu Asn Lys Glu Pro Leu Thr Leu Asp Val Glu
            675                 680                 685

Tyr Thr Glu Val Glu Val Thr Ser Pro Glu Pro His Gln Gly Leu Gly
690                 695                 700

Thr Lys Gly Thr Glu Thr Glu Thr Val Tyr Ser Glu Ile Arg Lys Ala
705                 710                 715                 720

Asp Pro Asp Phe Val Glu Asn Arg Tyr Ser Arg Thr Glu Gly Ser Leu
            725                 730                 735

Asp Gly Ser

<210> SEQ ID NO 4
<211> LENGTH: 740
<212> TYPE: PRT
<213> ORGANISM: Sus scrofa

<400> SEQUENCE: 4

Met Arg Leu Arg Trp Thr Gln Gly Gly Asn Met Trp Leu Gly Val Leu
1               5                   10                  15

Leu Thr Leu Gln Leu Cys Ser Ser Leu Glu Gly Gln Glu Asn Ser Phe
            20                  25                  30

Thr Ile Asn Ser Ile His Met Glu Met Leu Pro Gly Gln Glu Val His
            35                  40                  45

Asn Gly Glu Asn Leu Thr Leu Gln Cys Ile Val Asp Val Ser Thr Thr
    50                  55                  60

Ser Ser Val Lys Pro Gln His Gln Val Leu Phe Tyr Lys Asp Asp Val
65                  70                  75                  80

Leu Phe His Asn Val Ser Ser Thr Lys Asn Thr Glu Ser Tyr Phe Ile
            85                  90                  95

Ser Glu Ala Arg Val Tyr Asn Ser Gly Arg Tyr Lys Cys Thr Val Ile
            100                 105                 110

Leu Asn Asn Lys Glu Lys Thr Thr Ala Glu Tyr Lys Val Val Val Glu
            115                 120                 125

Gly Val Ser Asn Pro Arg Val Thr Leu Asp Lys Lys Glu Val Ile Glu
            130                 135                 140

Gly Gly Val Val Lys Val Thr Cys Ser Val Pro Glu Glu Lys Pro Pro
145                 150                 155                 160

Val His Phe Ile Ile Glu Lys Phe Glu Leu Asn Val Arg Asp Val Lys
            165                 170                 175
```

-continued

Gln Arg Arg Glu Lys Thr Ala Asn Asn Gln Asn Ser Val Thr Leu Glu
                180                 185                 190

Phe Thr Val Glu Glu Gln Asp Arg Val Ile Leu Phe Ser Cys Gln Ala
            195                 200                 205

Asn Val Ile Phe Gly Thr Arg Val Glu Ile Ser Asp Ser Val Arg Ser
        210                 215                 220

Asp Leu Val Thr Val Arg Glu Ser Phe Ser Asn Pro Lys Phe His Ile
225                 230                 235                 240

Ser Pro Lys Gly Val Ile Ile Glu Gly Asp Gln Leu Leu Ile Lys Cys
                245                 250                 255

Thr Ile Gln Val Thr His Gln Ala Gln Ser Phe Pro Glu Ile Ile Ile
            260                 265                 270

Gln Lys Asp Lys Glu Ile Val Ala His Ser Arg Asn Gly Ser Glu Ala
        275                 280                 285

Val Tyr Ser Val Met Ala Thr Val Glu His Asn Ser Asn Tyr Thr Cys
    290                 295                 300

Lys Val Glu Ala Ser Arg Ile Ser Lys Val Ser Ser Ile Met Val Asn
305                 310                 315                 320

Ile Thr Glu Leu Phe Ser Arg Pro Lys Leu Lys Ser Ser Ala Thr Arg
                325                 330                 335

Leu Asp Gln Gly Glu Ser Leu Arg Leu Trp Cys Ser Ile Pro Gly Ala
            340                 345                 350

Pro Pro Glu Ala Asn Phe Thr Ile Gln Lys Gly Gly Met Met Met Leu
        355                 360                 365

Gln Asp Gln Asn Leu Thr Lys Val Ala Ser Glu Arg Asp Ser Gly Thr
    370                 375                 380

Tyr Thr Cys Val Ala Gly Ile Gly Lys Val Val Lys Arg Ser Asn Glu
385                 390                 395                 400

Val Gln Ile Ala Val Cys Glu Met Leu Ser Lys Pro Ser Ile Phe His
                405                 410                 415

Asp Ser Gly Ser Glu Val Ile Lys Gly Gln Thr Ile Glu Val Ser Cys
            420                 425                 430

Gln Ser Ile Asn Gly Thr Ser Pro Ile Ser Tyr Gln Leu Leu Lys Gly
        435                 440                 445

Ser Asp Leu Leu Ala Ser Gln Asn Val Ser Ser Asn Glu Pro Ala Val
450                 455                 460

Phe Lys Asp Asn Pro Thr Lys Asp Val Glu Tyr Gln Cys Ile Ala Asp
465                 470                 475                 480

Asn Cys His Ser His Ala Gly Met Pro Ser Lys Val Leu Arg Val Lys
                485                 490                 495

Val Ile Ala Pro Val Glu Glu Val Lys Leu Ser Ile Leu Leu Ser Glu
            500                 505                 510

Glu Val Glu Ser Gly Gln Ala Ile Val Leu Gln Cys Ser Val Lys Glu
        515                 520                 525

Gly Ser Gly Pro Ile Thr Tyr Lys Phe Tyr Lys Glu Lys Glu Asn Lys
    530                 535                 540

Pro Phe His Gln Val Thr Leu Asn Asp Thr Gln Ala Ile Trp His Lys
545                 550                 555                 560

Pro Lys Ala Ser Lys Asp Gln Glu Gly Gln Tyr Tyr Cys Leu Ala Ser
                565                 570                 575

Asn Arg Ala Thr Pro Ser Lys Asn Phe Leu Gln Ser Asn Ile Leu Ala
            580                 585                 590

Val Arg Val Tyr Leu Ala Pro Trp Lys Lys Gly Leu Ile Ala Val Val

```
                595                 600                 605
Val Ile Ala Val Ile Ala Val Leu Leu Gly Ala Arg Phe Tyr
            610                 615                 620

Phe Leu Lys Lys Ser Lys Ala Lys Gln Met Pro Val Glu Met Cys Arg
625                 630                 635                 640

Pro Ala Ala Pro Leu Leu Asn Ser Asn Asn Glu Lys Thr Leu Ser Asp
                645                 650                 655

Pro Asn Thr Glu Ala Asn Arg His Tyr Gly Tyr Asn Glu Asp Val Gly
            660                 665                 670

Asn His Ala Met Lys Pro Leu Asn Glu Asn Lys Glu Pro Leu Thr Leu
            675                 680                 685

Asp Val Glu Tyr Thr Glu Val Glu Val Thr Ser Pro Glu Pro His Arg
            690                 695                 700

Gly Leu Gly Thr Lys Gly Thr Glu Thr Val Tyr Ser Glu Ile Arg Lys
705                 710                 715                 720

Ala Asp Pro Asp Leu Val Glu Asn Arg Tyr Ser Arg Thr Glu Gly Ser
                725                 730                 735

Leu Asp Gly Thr
            740

<210> SEQ ID NO 5
<211> LENGTH: 8
<212> TYPE: PRT
<213> ORGANISM: Artificial
<220> FEATURE:
<223> OTHER INFORMATION: Synthetic murine-derived CD31 peptide

<400> SEQUENCE: 5

Arg Val Phe Leu Ala Pro Trp Lys
1               5

<210> SEQ ID NO 6
<211> LENGTH: 8
<212> TYPE: PRT
<213> ORGANISM: Artificial
<220> FEATURE:
<223> OTHER INFORMATION: Synthetic murine-derived CD31 peptide

<400> SEQUENCE: 6

Lys Trp Pro Ala Leu Phe Val Arg
1               5

<210> SEQ ID NO 7
<211> LENGTH: 8
<212> TYPE: PRT
<213> ORGANISM: Artificial
<220> FEATURE:
<223> OTHER INFORMATION: Synthetic human-derived CD31 peptide

<400> SEQUENCE: 7

Arg Val Ile Leu Ala Pro Trp Lys
1               5

<210> SEQ ID NO 8
<211> LENGTH: 8
<212> TYPE: PRT
<213> ORGANISM: Artificial
<220> FEATURE:
<223> OTHER INFORMATION: Synthetic human-derived CD31 peptide
```

```
<400> SEQUENCE: 8

Lys Trp Pro Ala Leu Ile Val Arg
1               5
```

CD31 PEPTIDES

FIELD OF THE INVENTION

The present invention provides synthetic peptides corresponding and related to fragments of CD31 that favour endothelial physiologic functions while inhibiting platelet and leukocyte activation, and to their use in the treatment of disease. These peptides find use in treatment of inflammatory and thrombotic diseases, in particular when immobilised onto medical devices in contact with body fluids.

BACKGROUND

Thrombotic Disorders

In a healthy person, a homeostatic balance exists between procoagulant (clotting) forces and anticoagulant and fibrinolytic forces. Numerous genetic, acquired, and environmental factors can tip the balance in favor of coagulation, leading to the pathologic formation of thrombi in veins (e.g. deep vein thrombosis), arteries (e.g. atherothrombosis, myocardial infarction, ischemic stroke), or cardiac chambers. Thrombi can obstruct blood flow at the site of formation or detach and embolize to block a distant blood vessel (e.g. pulmonary embolism, stroke).

Accumulating evidence show that atherothrombosis, a world-leading life-threatening disease, is linked to inappropriate activation of blood leukocytes and platelets leading to a destructive inflammatory response within the vascular wall and thrombotic occlusion and/or rupture due the fibrinolytic cascade. Consequently, a restoration of the physiologic cell regulation at the interface between the blood and the vessel wall would represent an innovative therapeutic option to fight atherothrombosis.

Inflammatory and Autoimmune Disorders

Inflammatory disorders underlie a large number of human diseases. The immune system is often involved with inflammatory disorders, demonstrated in both allergic reactions and some myopathies, with many immune system disorders resulting in abnormal inflammation. Non-immune diseases with etiological origins in inflammatory processes include cancer, atherosclerosis, and ischaemic heart disease.

In autoimmune disorders, the immune system produces antibodies to an endogenous antigen. Antibody-coated cells, like any similarly coated foreign particle, activate the complement system, resulting in tissue injury. Autoimmune disorders include systemic lupus erythematodes (SLE), rheumatoid arthritis (RA), multiple sclerosis (MS), inflammatory bowel disease (IBD), Graves' disease and diabetes mellitus. Systemic vasculitis, venous chronic insufficiency and atherosclerosis-related vascular diseases are also comprised within autoimmune-inflammatory disorders in which the target tissue is the vascular wall and the nearby organs and tissues.

Several mechanisms may account for the body's attack on itself. Autoantigens may become immunogenic because they are altered chemically, physically, or biologically. Certain chemicals couple with body proteins, making them immunogenic (as in contact dermatitis). Drugs can produce several autoimmune reactions by binding covalently to serum or tissue proteins (see below). Photosensitivity exemplifies physically induced autoallergy: Ultraviolet light alters skin protein, to which the patient becomes allergic. In animal models, persistent infection with an RNA virus that combines with host tissues alters autoantigens biologically, resulting in an autoallergic disorder resembling SLE.

Most human autoimmune diseases are driven by antigen-specific, adaptive immune cells (T- and B-cell lymphocytes). T- and B-cell clones responding to specific antigenic epitopes are responsible for the initiation and/or the propagation of these diseases. Similarly, specific antigen-driven T- and B-cell responses are responsible for the rejection of organ allografts. In addition to the adaptive immune cells, cells of the innate immune system, which are not specific of a given antigen, are also involved in the pathogenesis of chronic inflammatory (autoimmune) disorders, such as granulocytes, monocyte-macrophages, dendritic cells and natural killer cells.

CD31 (PECAM-1)

CD31 is a single chain, homophilic transmembrane receptor exclusively and constitutively present on all endothelial cells, platelets and leukocytes. CD31 consists of a single chain 130-kDa glycoprotein comprising six Ig-like extracellular domains, a short transmembrane segment and a cytoplasmic tail. The cytoplasmic tail contains two important tyrosine-based motifs (around Y663 and Y686) that form specific docking sites for SH2-containing adaptor molecules that preferentially associate with phosphatases and act as ImmunoTyrosine-based Inhibitory Motif (ITIM)s. The structure of CD31 is shown in the table below.

| Domain | Position on SEQ ID No: 1 |
| --- | --- |
| Signal peptide | 1 to 27 |
| Extracellular domain | 28 to 601 |
| First Ig-like extracellular domain | 34 to 121 |
| Second Ig-like extracellular domain | 145 to 233 |
| Third Ig-like extracellular domain | 236 to 315 |
| Fourth Ig-like extracellular domain | 328 to 401 |
| Fifth Ig-like extracellular domain | 424 to 493 |
| Sixth Ig-like extracellular domain | 499 to 591 |
| Juxta-membrane domain | 592 to 601 |
| Transmembrane domain | 602 to 620 |
| Cytoplasmic domain | 621 to 738 |

The intracellular CD31 ITIMs are not phosphorylated in resting conditions because CD31 does not possess an intrinsic kinase activity. CD31 molecules bind to each other via a trans-homophilic liaison of the Ig-like domains 1-2 between interacting cells. This trans-homophilic binding is required to trigger the clustering of the CD31 molecules on the membrane plane, which in turn requires a cis-homophilic juxtamembrane sequence. The phosphorylation of the CD31 intracellular ITIMs becomes then possible because its ITIMs can be exposed to the activity of the tyrosine kinases that are carried close by other cluster-associated membrane receptors (such for instance the T cell receptor). The phosphorylation of the intracellular ITIMs triggers the recruitment and activation of intracellular SH2-containing phosphatases. Depending on the signalling adaptors associated to the closest membrane receptor, the activation of SH2-containing phosphatases can lead to either the activation of signalling cascades (e.g. GAB/ERK/MAPK, driving adherence and growth of endothelial cells, foxp3 expression and differentiation of lymphocytes into the regulatory phenotype, driving active cell-cell detachment) or their inhibition (e.g. JAK/STAT, preventing leukocyte and platelet activation). Accordingly, the function of CD31 varies upon the cell type.

The presence of CD31 at high density at endothelial intercellular borders has previously led to the hypothesis that CD31 functions as a cell adhesion molecule in endothelial cells, involved in leukocyte extravasation. However, CD31 is excluded from the tight endothelial cell junctions and experimental evidence rather show it prevents leukocyte extravasation since the latter increases in the CD31-deficient mice. Endothelial CD31 becomes tyrosine-phosphorylated upon mechanical stress and its function is necessary to stabilize the endothelial structure and angiogenesis.

CD31 becomes tyrosine-phosphorylated following activation and aggregation of platelets. This represents a negative feedback mechanism because CD31 clustering inhibits platelet aggregation and thrombus formation by uncoupling signal transduction though several activatory receptors. The immunoregulatory properties of CD31 are supported by the fact that CD31 signalling drives mutual repulsion of blood leukocytes and modulates the balance between inhibitory and stimulatory signals of both innate and adaptive immune cells. Mechanical engagement of the distal Ig-like extracellular domains of CD31 induces outside-in inhibitory signalling triggered by the phosphorylation of its ITIMs, and the recruitment and activation of SH2-containing phosphatases.

Zehnder et al. (1995, Blood. 85(5):1282-8) identified a CD31 antibody that inhibited the mixed lymphocyte reaction (MLR) in a specific and dose-dependent manner. They further found that a CD31 peptide corresponding to the epitope of this antibody, i.e. to the 23 membrane-proximal amino acids of CD31, strongly inhibited the MLR. They hypothesized that the 23 membrane-proximal amino acids of CD31 constitutes a functionally important region, and that the CD31 peptide interferes with lymphocyte activation by competing for binding epitopes. However, Zehnder et al. failed to teach whether CD31-mediated signaling is activated or inhibited by the CD31 peptide.

Chen et al. (1997, Blood. 89(4):1452-9) showed that this peptide delayed onset of graft-versus-host disease (GVHD) and increased long-term survival in a murine model of the disease. They hypothesized that the CD31 peptide inhibits a common pathway in T-cell activation. Again, Chen et al. failed to elucidate the role played by the CD31 peptide in T-cell activation. In particular, these previous works did not assess the putative effect of the peptide on the CD31 signaling cascade and more precisely on the phosporylation state of the CD31 ITIMs.

By a yet unknown mechanism, CD31 is "lost" on certain circulating lymphocytes. Its loss is observed upon lymphocyte activation and it has been recently shown that the absence of lymphocyte CD31 signalling, in turn, heightens the pathologic immune responses involved in the development of atherothrombosis.

A soluble form of CD31, due to a variant transcript lacking the transmembrane segment, has also been reported and therefore it is currently thought that the individual amount of circulating CD31 is genetically determined. Consequently, a number of previous studies have attempted to find a correlation between plasma levels of soluble CD31 and the risk of atherothrombosis or other inflammatory diseases. However, independently of the specific genetic polymorphisms analyzed, data showed a broad range of plasma CD31 values and the results of these different studies were contradicting.

There is therefore a need for better understanding the biological function of CD31. This would allow the provision of more efficient therapeutics for the treatment of diseases linked with T-cell activation.

The inventors have previously reported that the assumed loss of CD31 on activated/memory T lymphocytes is actually incomplete and results from shedding of CD31 between the 5$^{th}$ and the 6$^{th}$ extracellular Ig-like domains (described in international patent publication WO2010/000741). The shed extracellular domain of CD31 (further referred to as "shed CD31") is then released into the circulation, where it is present together with a soluble splice variant of CD31. In addition, they have shown that a high risk of atherothrombosis is linked with the increase in shed CD31 and decrease in splice variant CD31 in the circulation, and not with the total level of circulating CD31.

The finding that CD31 is not lost on blood lymphocytes but only cleaved provided a unique opportunity to rescue its physiological immunoregulatory function by targeting the residual portion of the molecule.

The inventor's previous work showed that peptides corresponding to juxtamembrane amino acids of the ectodomain of CD31 are able to rescue the physiological immunoregulatory function of CD31, even in patients having apparently lost CD31 from the surface of their circulating T lymphocytes. They demonstrated that such peptides are capable of preventing disease progression and aneurysm formation in a mouse model for atherosclerosis. The peptides have unique properties compared to soluble forms of CD31 comprising all or most Ig-like domains of CD31. Indeed, such peptides are highly homophilic since they have a Kd of $10^{-7}$M, as assessed by BIAcore analysis. Hence they are able to engage CD31 signaling by bridging the membrane juxta-proximal part of extracellular CD31 that remains expressed after its cleavage, via a strong homo-oligomerization. In contrast to this, alternatively spliced soluble CD31 lacks the first 10 membrane juxta-proximal amino acids and shows weak homophilic binding with the 23-mer peptide (Kd of 17 μM, as assessed by BIAcore analysis). Furthermore, in vitro, only the peptides identified by the inventors are capable of engaging the ITIM pathway downstream of the truncated isoform of CD31, and are thus capable of restoring CD31 signaling in T lymphocytes having apparently lost CD31.

DESCRIPTION OF THE INVENTION

The inventors have identified a specific 8 amino acid peptide within the membrane juxta-proximal part of extracellular CD31, which is of particular utility in inhibiting platelet and leukocyte activation and in treatment of a thrombotic or an inflammatory disorders. The fact that this sequence is soluble in water is an advantage on the pharmacological point of view. They have further shown that peptide sequences corresponding to this 8 amino-acid fragment comprising inversions, and/or unnatural aminoacids, such as D-enantiomers, also retain these activities or demonstrate improved activity. Incorporation of unnatural aminoacids in peptides intended for therapeutic use is of utility in increasing the stability of the peptide, in particular in vivo stability.

The invention thus provides an peptide consisting of the amino acid sequence of amino acids 582 to 589 of murine CD31 SEQ ID NO: 2 or the amino acid sequence corresponding to this sequence in another mammalian CD31, such as a human CD31 (SEQ ID NO 1) porcine CD31 (SEQ ID NO 4) or bovine CD31 (SEQ ID NO 3). Corresponding sequences may be identified by referring to the alignment of FIG. 1 or any other alignments performed as described herein. Thus, the invention also provides an isolated peptide consisting of the amino acid sequence of amino acids 593- to 600 of SEQ ID NO: 1. The invention also provides peptides consisting of the above-described sequences wherein the position of two or more amino acids is inverted or displaced. Also provided are peptides as described above wherein one or more amino acids are in the D-enantiomer form. Preferably, the peptide is an isolated peptide.

Preferably, the peptide of the invention is soluble in an organic or nonorganic solvent, such as water.

Also provided are peptides comprising a sequence consisting of a fragment of said the amino acid sequence of amino acids 582 to 589 of SEQ ID NO: 2 or the amino acid sequence corresponding to this sequence in another mammalian CD31, such as a human CD31 (SEQ ID NO 1) porcine CD31 (SEQ ID NO 4) or bovine CD31 (SEQ ID NO 3). Corresponding sequences may be identified by referring to the alignment of FIG. 1 or any other alignments performed as described herein. A 'fragment' refers to a sequence of consecutive amino acids. For example, said fragment may be a fragment of 1, 2, 3, 4, 5, 6 or 7 amino acids.

The CD31 peptide of the invention may comprise a chirality change such as e.g. replacement of one or more naturally occurring amino acids (L enantiomer) with the corresponding D-enantiomers. D-enantiomers of amino acids are referred to by the same letter as their corresponding L-enantiomer, but in lower case. Thus, for example, the L-enantiomer of arginine is referred to as 'R', while the D-enantiomer is referred to as 'r'. For example, 1, 2, 3, 4, 5, 6, 7 or 8 of the amino acids in the peptide may be in the D-enantiomer form. The peptides may comprise the modified or non-natural amino acids, as described below.

The CD31 peptide of the invention may comprise an inverted sequence, namely an inversion of the amino acid chain (from the C-terminal end to the N-terminal end). The entire amino acid sequence of the peptide may be inverted, or a portion of the amino acid sequence may be inverted. For example, a consecutive sequence of 2, 3, 4, 5, 6, 7 or 8 amino acids may be inverted. Reference herein to 'inverted' amino acids refers to inversion of the sequence of consecutive amino acids in the sequence. The peptide may comprise a retro-inversion in which one or more naturally-occurring amino acids (L-enantiomer) are replaced with the corresponding D-enantiomers, together with an inversion of the amino acid chain (from the C-terminal end to the N-terminal end).

The peptide of the invention may thus have the sequence:
H-RVFLAPWK-OH (SEQ ID NO 5), corresponding to the amino acid sequence of amino acids 582 to 589 of SEQ ID NO: 2; (P8F)
H-kwpalfvr-OH (SEQ ID NO 6), corresponding to the inverted sequence of amino acids 582 to 589 of SEQ ID NO: 2 in D-enantiomer form, namely a retro-inversion of said sequence; (P8RI)
H-RVILAPWK-OH (SEQ ID NO 7), corresponding to the amino acid sequence of amino acids 593-600 of SEQ ID NO: 1;
H-kwpalivr-OH (SEQ ID NO 8), corresponding to the inverted sequence of amino acids 593-600 of SEQ ID NO: 1 in D-enantiomer form, namely a retro-inversion of said sequence.

In preferred embodiments, the peptide of the invention commences with the motif RV.

Also provided are isolated nucleic acids encoding the peptides of the invention, and pharmaceutical compositions comprising said peptides, as described below.

In addition to the CD31 fragment, the peptide may optionally comprise sequences heterologous to CD31. These heterologous sequences may e.g. correspond to a carrier molecule such as the Keyhole Limpet Hemocyanin (KLH), bovine serum albumin (BSA), ovalbumin (OVA), thyroglobulin (THY) or the multiple antigenic peptide (MAP). Thus the invention provides peptides comprising a peptide of the invention in addition to heterologous sequence.

The sequence of CD31 peptides according to the invention is preferably derived from the sequence of human or murine CD31. However, the sequence of CD31 may be derived from any non-human mammalian CD31 sequence. FIG. 1 shows an alignment between the human, murine, bovine and pig CD31 sequences. The person skilled in the art can easily identify the corresponding sequence in another non-human mammalian CD31 protein by performing a sequence alignment with the sequences shown in FIG. 1. Methods for sequence alignment and determination of sequence identity are well known in the art, for example using publicly available computer software such as BioPerl, BLAST, BLAST-2, CS-BLAST, FASTA, ALIGN, ALIGN-2, LALIGN, Jaligner, matcher or Megalign (DNASTAR) software and alignment algorithms such as the Needleman-Wunsch and Smith-Waterman algorithms.

CD31 peptides according to the invention may have the biological activity of exerting a dose-dependent inhibition of T-cell proliferation in vitro and/or of inhibiting the mixed-lymphocyte reaction (MLR; inhibition of platelet aggregation; inhibition of platelet activatin; inhibition of thrombin generation by platelets and/or inhibition of VCAM-1 expression of endothelial cells. Their biological activity may for example be measured as described in Example 1, 2, 3 or 4 or in Zehnder et al. 1995, Blood. 85(5):1282-8, Fornasa et al. 2010, J Immunol 184: 6585-6591; Fornasa et al, 2012, Cardiovascular Research 94: 30-37.

The T-cell proliferation assay may comprise comparing the radioactivity incorporated into T-cells cultured either in the presence or in the absence of the compound to be tested. This assay may for example be performed as follows:
providing a multi-well plate comprising complete medium supplemented with anti-CD3 antibodies;
supplementing the wells with increasing concentrations of the compound to be tested;
plating peripheral blood mononuclear cells (or spleen cells, or lymph node cells);
culturing the cells for about 72 hours;
adding ($^3$H) thymidine and culturing the cells for about 16 hours;
measuring the radioactivity; and
comparing the radioactivity measured in the presence of the compound to be tested with the radioactivity measured in the absence of said compound, and/or in the presence of a reference compound, and/or in the presence of a negative control.

Alternatively, the T-cell proliferation assay may comprise the use of carboxyfluorescein diacetate succinimidyl ester (CFSE), as described in Nature Protocols, 2007, 2: 2049-2056 and in Fornasa et al, 2012, Cardiovascular Research 94: 30-37:
Incorporate optimum amount of the fluorescent probe (CFSE) in peripheral blood mononuclear cells (or spleen cells, or lymph node cells) in the presence of complete culture medium
providing a multi-well plate comprising, CFSE-stained cells and the stimulus (anti-CD3 antibodies)
supplementing the wells with increasing concentrations of the compound to be tested;
Comparing the number of daughter cells (proliferation) based on the intensity of the fluorescent staining by flow cytometry Alternatively, the leukocyte activation may be assessed by comparing expression levels of the early activation marker CD69 leukocytes (blood mononuclear cells or spleen cells, or lymph node cells) cultured either in the presence or in the absence of the compound to be tested. This assay may for example be performed as follows:
- providing (blood mononuclear cells or spleen cells, or lymph node cells) or purified leukocyte subpopulation;
- stimulating said cells by addition of an appropriate stimulus (anti-CD3 purified antibodies and bone marrow derived dendritic cells; or LPS or a lectin such as ConA, PHA, PWM);
- culturing the cells for up to 48 hours; and
- analyzing said cells for the expression of the early activation marker CD69, e.g. by flow cytometry; and
- comparing CD69 expression in the presence of the compound to be tested.

CD31 peptides according to the invention may be prepared by any well-known procedure in the art, such as solid phase synthesis, liquid phase synthesis or genetic engineering. As a solid phase synthesis, for example, the amino acid corresponding to the C-terminus of the peptide to be synthesized is bound to a support which is insoluble in organic solvents, and by alternate repetition of reactions, one wherein amino acids with their amino groups and side chain functional groups protected with appropriate protective groups are condensed one by one in order from the C-terminus to the N-terminus, and one where the amino acids bound to the resin or the protective group of the amino groups of the peptides are released, the peptide chain is thus extended in this manner. After synthesis of the desired peptide, it is subjected to the deprotection reaction and cut out from the solid support.

The CD31 peptides of the invention may optionally comprise additional chemical modifications, optionally aimed at improving their stability and/or their bioavailability. Such chemical modifications aim at obtaining peptides with increased protection of the peptides against enzymatic degradation in vivo, and/or increased capacity to cross membrane barriers, thus increasing its half-life and maintaining or improving its biological activity. Any chemical modification known in the art can be employed according to the present invention. Such chemical modifications include but are not limited to:
- modifications to the N-terminal and/or C-terminal ends of the peptides such as e.g. N-terminal acylation (preferably acetylation) or desamination, or modification of the C-terminal carboxyl group into an amide or an alcohol group;
- modifications at the amide bond between two amino acids: acylation (preferably acetylation) or alkylation (preferably methylation) at the nitrogen atom or the alpha carbon of the amide bond linking two amino acids;
- modifications at the alpha carbon of the amide bond linking two amino acids such as e.g. acylation (preferably acetylation) or alkylation (preferably methylation) at the alpha carbon of the amide bond linking two amino acids;
- of the amino acid chain (from the C-terminal end to the N-terminal end);
- azapeptides, in which one or more alpha carbons are replaced with nitrogen atoms; and/or
- betapeptides, in which the amino group of one or more amino acid is bonded to the β carbon rather than the α carbon.

Polypeptides include amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini, it will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from natural post-translational processes or may be made by synthetic methods. Modifications include acetylation, acylation, ADP-ribosylation, araidation, covalent attachment of flavin, covalent attachment of a heme moiety, covalent attachment of a nucleotide or nucleotide derivative, covalent attachment of a lipid or lipid derivative, covalent attachment of phosphatidyl inositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemizaiion, selenoyiation, sulfation, transfer-RNA mediated addition of amino acids to proteins such as arginyiation, and ubiquitination.

By an "isolated" peptide, it is intended that the peptide is not present within a living organism, e.g. within human body. However, the isolated peptide may be part of a composition or a kit. The isolated peptide is preferably purified.

The compounds of the invention may be produced by any well-known procedure in the art, including chemical synthesis technologies and recombinant technologies.

Examples of chemical synthesis technologies are solid phase synthesis and liquid phase synthesis. As a solid phase synthesis, for example, the amino acid corresponding to the C-terminus of the peptide to be synthesized is bound to a support which is insoluble in organic solvents, and by alternate repetition of reactions, one wherein amino acids with their amino groups and side chain functional groups protected with appropriate protective groups are condensed one by one in order from the C-terminus to the N-terminus, and one where the amino acids bound to the resin or the protective group of the amino groups of the peptides are released, the peptide chain is thus extended in this manner. Solid phase synthesis methods are largely classified by the tBoc method and the Fmoc method, depending on the type of protective group used. Typically used protective groups include tBoe (t-butoxycarbonyl), Cl-Z (2-chlorobenzyloxycarbonyl), Br-Z (2-bromobenzyloyycarbonyl), Bzl (benzyl), Fmoc (9-fluorenylmcthoxycarbonyl), Mbh (4,4'-dimethoxydibenzhydryl), Mtr (4-methoxy-2,3,6-trimethylbenzenesulphonyl), Trt (trityl), Tos (tosyl), Z (benzyloxycarbonyl) and Clz-Bzl (2,6-dichlorobenzyl) for the amino groups; NO2 (nitro) and Pmc (2,2,5,7,8-pentamethylchromane-6-sulphonyl) for the guanidino groups); and tBu (t-butyl) for the hydroxyl groups). After synthesis of the desired peptide, it is subjected to the de-protection reaction and cut out from the solid support. Such peptide cutting reaction may be carried with hydrogen fluoride or tri-fluoromethane sulfonic acid for the Boc method, and with TFA for the Fmoc method.

Alternatively, the peptide may be synthesized using recombinant techniques. In this case, a nucleic acid encoding a peptide according to the invention (further referred to as "a nucleic acid according to the invention") is cloned into an expression vector. The nucleic acid of the invention is preferably placed under the control of expression signals (e.g. a promoter, a terminator and/or an enhancer) allowing its expression. The expression vector is then transfected into a host cell (e.g. a human, CHO, mouse, monkey, fungal or bacterial host cell), and the transfected host cell is cultivated under conditions suitable for the expression of the peptide.

The method of producing the peptide may optionally comprise the steps of purifying said peptide, chemically modifying said peptide, and/or formulating said peptide into a pharmaceutical composition.

Preferably, the peptide of the invention is soluble in an organic or nonorganic solvent, for example water or aqueous buffer such as NaCl 9 g/L, PBS, Tris or Tris-phosphate. Thanks to such solubility, the peptide may be dissolved in water at a concentration of, for example, 1 micromolar, 10 micromolar, 50 micromolar, 100 micromolar, 500 micromolar, 1 mM, 50 mM, 100 mM or more.

Use of CD31 Peptides for the Treatment of Thrombotic and Inflammatory Disorders

It has been found that CD31 peptides according to the invention are capable of activating CD31-mediated signaling, even in CD31$^-$ (i.e. CD31$^{shed}$)T lymphocytes. In addition, such peptides are capable of preventing disease progression and aneurysm formation in a mouse model for atherosclerosis, and improving clinical score in a mouse model of multiple sclerosis.

The invention therefore also provides a peptide of the invention for use in activating CD31-mediated signaling. These peptides preferably exert a dose-dependent inhibition of T-cell proliferation in vitro. The activation of CD31-mediated signaling may be an in vitro or an in vivo activation. Also provided are methods of activating CD31-mediated signalling using the peptides of the invention, in vitro or in vivo. The in vivo method may be a method of treatment as defined below.

As used throughout the present specification, the term "CD31-mediated signaling" refers to a signaling pathway in which CD31 is involved. Such pathways are well known in the art and include those described e.g. in Newman and Newman (2003 Arterioscler Thromb Vasc Biol 23:953-964) and in Newton-Nash and Newman (1999. J Immunol 163: 682-688).

The invention therefore also provides a peptide of the invention for use in the treatment of a thrombotic or an inflammatory disorder. These peptides preferably exert a dose-dependent inhibition of T-cell proliferation in vitro. The activation of CD31-mediated signaling may be an in vitro or an in vivo activation. Also provided are methods of treatment of a thrombotic or an inflammatory disorder using the peptides of the invention, preferably comprising administration of said peptides to an individual in need thereof.

As used throughout the present specification, the term "thrombotic disorder" includes but is not limited to atherothrombosis, atherosclerosis, acute coronary syndrome, ischemic stroke, peripheral arterial disease and abdominal aortic aneurysm.

As used throughout the present specification, the term "inflammatory disorder" includes but is not limited to chronic inflammatory diseases such as inflammatory bowel disease, psoriasis, atopic dermatitis, cerebral amyloid angiopathy, vasculitis. The term also includes autoimmune disorders, including but not limited to rheumatoid arthritis (RA), multiple sclerosis (MS), inflammatory bowel disease (IBD), systemic lupus erythematodes (SLE), Graves' disease and diabetes mellitus. Other conditions such as acute and chronic grant rejection including graft versus host disease (GVHD) and septic shock may be encompassed by the term. For example, the peptides of the invention may be used to treat septic shock (optionally in combination with antibiotic therapy, e.g. large spectrum antibiotic therapy) and in transplantation such as bone marrow, kidney, heart, liver or lung transplantation.

In a preferred embodiment of the invention, said thrombotic or inflammatory disorder is associated with a loss of CD31$^+$ T lymphocyte phenotype. Indeed, it has been surprisingly found that CD31 peptides restore CD31 signaling even in individuals with a CD31$^-$ T lymphocytes phenotype. Therefore, in the context of the present invention, CD31 peptides are preferably used to treat a subgroup of individuals and/or patients having a CD31$^-$ T lymphocytes phenotype.

As used herein, the term "CD31$^-$ T lymphocyte phenotype" is used interchangeably with the term "CD31$^{shed}$ T lymphocyte phenotype". These terms refer to the phenotype of an individual having apparently lost CD31 on its circulating T cells when conventional prior art methods for detecting CD31, e.g. such as those described in Stockinger et al. (Immunology, 1992, 75(1):53-8), Demeure et al. (Immunology, 1996, 88(1):110-5), Caligiuri et al. (Arterioscler Thromb Vasc Biol, 2005, 25(8):1659-64) or Caligiuri et al. (Arterioscler Thromb Vasc Biol, 2006, 26(3):618-23) are used. In such methods, the antibody used for detecting CD31 binds to an epitope located on any one of the 1$^{st}$ to the 5$^{th}$ extracellular Ig-like domains.

Preferably, individuals having a CD31$^-$ T lymphocyte phenotype, meaning that at least 50%, 60%, 65%, 70%, 75%, 80%, 90% or 95% of their circulating T lymphocytes are CD31$^{shed}$ lymphocytes. Either the plasma concentration of T-cell-derived truncated CD31 or the frequency of CD31$^-$ T lymphocytes, compared to CD31$^+$ T lymphocytes, may be measured.

The invention is also directed to a method of treating or preventing a thrombotic or an inflammatory disorder comprising the step of administering an effective amount of a peptide as described herein, or a nucleic coding therefore, to an individual in need thereof. Said individual in need thereof preferably suffers from or is at risk of suffering from a thrombotic or an inflammatory disorder. Most preferably, said individual has a CD31$^-$ T lymphocytes phenotype.

By "effective amount", is meant an amount sufficient to achieve a concentration of peptide, which is capable of preventing, treating or slowing down the disease to be treated. Such concentrations can be routinely determined by those of skilled in the art. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like. It will also be appreciated by those of stalled in the art that the dosage may be dependent on the stability of the administered peptide.

The individuals to be treated in the frame of the invention are preferably human individuals. However, the veterinary use of CD31 peptides for treating other mammals is also contemplated by the present invention.

Pharmaceutical Compositions

The CD31 peptides described herein may be formulated into a pharmaceutical composition. Thus the invention contemplates a pharmaceutical composition comprising any one of the above CD31 peptides and a physiologically acceptable carrier. Physiologically acceptable carriers can be prepared by any method known by those skilled in the art.

Pharmaceutical compositions comprising at least one peptide of the invention include all compositions wherein the peptide(s) are contained in an amount effective to achieve the intended purpose. In addition, the pharmaceutical compositions may contain suitable pharmaceutically acceptable carriers comprising excipients and auxiliaries, which facilitate processing of the active compounds into preparations which can be used pharmaceutically. Suitable pharmaceutically acceptable vehicles are well known in the art and are described for example in Remington's Pharmaceutical Sciences (Mack Publishing Company, Easton, USA, 1985), which is a standard reference text in this field. Pharmaceutically acceptable vehicles can be routinely selected in accordance with the mode of administration, solubility and stability of the peptides. For example, formulations for intravenous administration may include sterile aqueous solutions which may also contain buffers, diluents and other suitable additives. The use of biomaterials and other polymers for drug delivery, as well the different techniques and models to validate a specific mode of administration, are disclosed in literature.

The peptides of the present invention may be administered by any means that achieve the intended purpose. For example, administration may be achieved by a number of different routes including, but not limited to subcutaneous, intravenous, intradermal, intramuscular, intraperitoneal, intracerebral, intrathecal, intranasal, oral, rectal, transdermal, buccal, topical, local, inhalant or subcutaneous use.

The peptides of the present invention may be attached to a solid support, such as a stent. For example, the peptides may be covalently grafted onto a polymer or directly onto an aminated metal surface for use on intravascular prostheses such as stents, arterial tubes and mechanical valves. The immobilised peptide would prevent platelet and leukocyte adherence and activation to the prosthesis while promoting the acceptance/integration of the device in the body by favouring endothelial cell attachment and growth.

The latter use could include endovascular prostheses, such as tubes and stents, artificial heart valves, bone and dental prostheses Dosages to be administered depend on individual needs (which may be quantified by measuring cell-specific truncated CD31 in the plasma with using our bead-based method), on the desired effect and the chosen route of administration. It is understood that the dosage administered will be dependent upon the age, sex, health, and weight of the recipient, concurrent treatment, if any, frequency of treatment, and the nature of the effect desired. The total dose required for each treatment may be administered by multiple doses or in a single dose.

Depending on the intended route of delivery, the compounds may be formulated as liquid (e.g., solutions, suspensions), solid (e.g., pills, tablets, suppositories) or semisolid (e.g., creams, gels) forms or immobilised on the surface of a medical device.

In a preferred embodiment, the compositions are presented in unit dosage forms to facilitate accurate dosing. The term "unit dosage forms" refers to physically discrete units suitable as unitary dosages for human subjects and other mammals, each unit containing a pre-determined quantity of active material calculated to produce the desired therapeutic effect, in association with a suitable pharmaceutical excipient. Typical unit dosage forms include pre-filled, pre-measured ampoules or syringes of the liquid compositions or pills, tablets, capsules or the like in the case of solid compositions. In such compositions, the compound of the invention is usually a minor component (from about 0.1 to about 50% by weight or preferably from about 1 to about 40% by weight) with the remainder being various vehicles or carriers and processing aids helpful for forming the desired dosing form.

The compounds of this invention can also be administered in sustained release forms or from sustained release drug delivery systems.

The expression "physiologically acceptable" is meant to encompass any carrier, which does not interfere with the effectiveness of the biological activity of the active ingredient and that is not toxic to the host to which is administered. For example, for parenteral administration, the above active ingredients may be formulated in unit dosage form for injection in vehicles such as saline, dextrose solution, serum albumin and Ringer's solution.

Besides the pharmaceutically acceptable carrier, the compositions of the invention can also comprise minor amounts of additives, such as stabilizers, excipients, buffers and preservatives.

The invention also contemplates a pharmaceutical composition comprising a nucleic acid encoding the peptide of the invention in the frame of e.g. a treatment by gene therapy. In this case, the nucleic acid is preferably present on a vector, on which the sequence coding for the peptide is placed under the control of expression signals (e.g. a promoter, a terminator and/or an enhancer) allowing its expression. The vector may for example correspond to a viral vector such as an adenoviral or a lentiviral vector.

The invention further provides kits comprising a pharmaceutical composition comprising a CD31 peptide of the invention and instructions regarding the mode of administration. These instructions may e.g. indicate the medical indication, and/or the route of administration, and/or the dosage, and/or the group of patients to be treated.

Prevention and Treatment

'Treatment' includes both therapeutic treatment and prophylactic or preventative treatment, wherein the object is to prevent or slow down the targeted pathologic condition or disorder. Those in need of treatment include those already with the disorder as well as those prone to have the disorder or those in whom the disorder is to be prevented. The terms 'therapy', 'therapeutic', 'treatment' or 'treating' include reducing, alleviating or inhibiting or eliminating the symptoms or progress of a disease, as well as treatment intended to reduce, alleviate, inhibit or eliminate said symptoms or progress. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, methods and compositions of the invention are used to delay development of a disease or disorder or to slow the progression of a disease or disorder.

Preferably, an effective amount, preferably a therapeutically effective amount of the protein or vector of the invention is administered. An 'effective amount' refers to an amount effective, at dosages and for periods of time necessary, to achieve the desired therapeutic or prophylactic result. The effective amount may vary according to the drug or prodrug with which the protein or vector is co-administered.

A 'therapeutically effective amount' of a peptide of the invention may vary according to factors such as the disease state, age, sex, and weight of the individual, and the ability of the protein, to elicit a desired therapeutic result. A therapeutically effective amount encompasses an amount in which any toxic or detrimental effects of the protein are outweighed by the therapeutically beneficial effects. A therapeutically effective amount also encompasses an amount sufficient to confer benefit, e.g., clinical benefit.

Throughout the specification, terms such as 'comprises', 'comprised', 'comprising' and can have the meaning attributed to them in most patent jurisdictions, preferably in the jurisdiction in question; e.g. they can mean 'includes', 'included', 'including', etc. Terms such as 'consisting of' 'consisting essentially of' and 'consists essentially of' have the meaning ascribed to them in most patent jurisdictions, preferably in the jurisdiction in question; e.g., they may imply the exclusion of all, most, or all but a negligible amount of other elements, or they may allow for elements not explicitly recited, but exclude elements that are found in the prior art or that affect a basic or novel characteristic of the invention.

The term 'about' as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The invention will now be described in more detail by means of the following non-limiting figures and examples. All references cited herein, including journal articles or abstracts, published or unpublished patent application, issued patents or any other references, are entirely incorporated by reference herein, including all data, tables, figures and text presented in the cited references.

BRIEF DESCRIPTION OF THE FIGURES

FIG. 1 shows an alignment between the amino acid sequences of human, mouse, pig and bovine CD31. The sequence defined by amino acids 593 to 600 of SEQ ID NO: 1 (human CD31) and the corresponding sequence in mouse, pig and bovine CD31 is indicated by a line above the sequence.

FIG. 4: Representative thrombograms; FIG. 5: Velocity index of thrombin activity, calculated as Peak/Time to peak-LagTime, was significantly reduced in P8RI vs Bare and Control wells. FIG. 6: The concentration of soluble P-selectin (sCD62P), released by platelets, was significantly reduced in the supernatant of P8RI-coated wells. Data are from 8 independent experiments, *$p<0.01$

BRIEF DESCRIPTION OF THE SEQUENCE LISTING

SEQ ID NO: 1 corresponds to the sequence of human CD31.

SEQ ID NO: 2 corresponds to the sequence of murine CD31.

SEQ ID NO: 3 corresponds to the sequence of bovine CD31.

SEQ ID NO: 4 corresponds to the sequence of pig CD31.

SEQ ID NO: 5 corresponds to the P8F peptide. H-RV-FLAPWK-OH

SEQ ID NO: 6 corresponds to the P8RI peptide. H-kw-palfvr-OH

SEQ ID NO: 7 corresponds to the human equivalent of the P8F peptide. H-RVILAPWK-OH SEQ ID NO: 8 corresponds to the human equivalent of the P8RI peptide H-kwpalivr-OH

EXAMPLES

Example 1

Effect on T-Cell Activation

Figure 2:
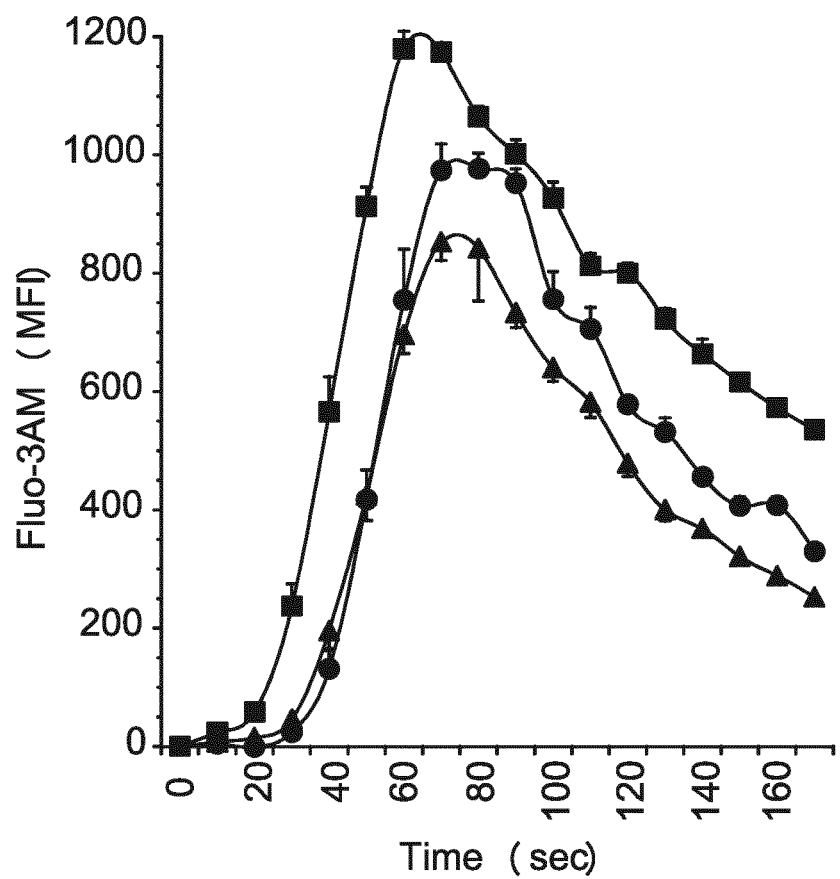
FIG. 2 shows the effect of P8F (SEQ ID NO 5) and P8R1 (SEQ ID NO 6) peptides on T-cell activation. Jurkat T cells were preincubated with the fluo 3-AM calcium probe and stimulated by cross-linking the TCR with anti-CD3 antibodies and secondary antibody F(ab')2 fragments. The figure shows the effect of 60 μg/ml of each peptide on calcium mobilization following TCR stimulation as follows: No peptide control (squares), P8F (SEQ ID NO 5) peptide (circles) and P8RI (SEQ ID NO 6) peptide (triangles).
Figure 3:
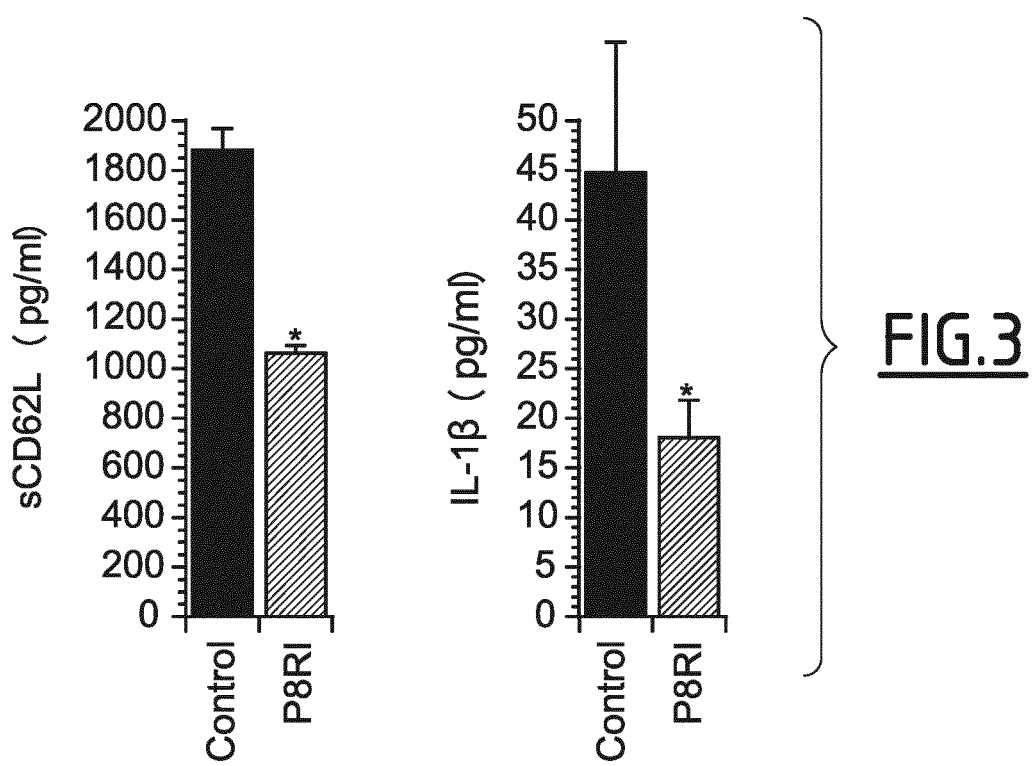
FIG. 3 shows that immobilised P8RI (SEQ ID NO:6) onto aminated solid surfaces inhibits leukocyte adherence and activation. Peripheral blood mononuclear cells ($5\times10^5$ cells/ml) were transferred in P8RI-coated and control Immulon® wells and stimulated with 1.mu.g/ml LPS for 60'. Control wells were coated with acetic acid (with EDC/S-NHS) as irrelevant source of COOH groups (Control) or left uncoated (Bare). Left, after 3 washes with PBS, Control wells contained several adherent leukocytes at variance with P8RI wells in which leukocytes were virtually absent. Right, soluble L-selectin (sCD62L) and interleukin-1β released from LPS-activated leukocytes (analyzed by cytometric beads, CBA®), were significantly reduced in P8RI-coated wells. *$p<0.05$ vs Control. Scale bar=100 μm

Jurkat T cells ($10\times10^6$/ml) were preincubated with the fluo 3-AM calcium probe and stimulated by cross-linking the TCR with anti-CD3 antibodies and secondary antibody F(ab')2 fragments. FIG. 2 shows continuous flow cytometry acquisition before and after addition of the stimulus±the peptides. As shown in the figure, the presence of 60 µg/ml of P8RI (H-kwpalfvr-OH) and P8F (H-RVFLAPWK-OH) lead to a delayed and reduced intracellular calcium mobilization (as determined by the median fluorescence intensity (FMI) of the fluo-3AM probe, following TCR stimulation of Jurkat cells.

Example 2

Effect of the Soluble Peptide on Platelet Aggregation

The microcapillaries of Vena8 Fluoro+™ biochip (400 µm width×100 µm depth×20 mm length, Cellix) were coated with 2.5 mg/ml insoluble horse type I collagen overnight at 4° C. and then blocked with 0.1% HSA for 1 hour at room temperature. Human peripheral whole blood, anticoagulated with P-PACK (a direct thrombin inhibitor, non-chelating agent) was labeled with 5 µM DiOC6 for 10 minutes before perfusion with the Cellix pump at 1500 seconds$^{-1}$ through the coated capillaries. The interaction of platelets with the matrix was viewed in real time under a fluorescence microscope and was saved for off-line analysis. The surface covered by aggregated platelets was analyzed frame by frame (24 frames/s) over the first 5 minutes and expressed as coverage %. Soluble P8RI (H-kwpalfvr-OH) and P8F (H-RVFLAPWK-OH) were both shown to inhibit human platelet aggregation in a dose dependent manner.

Example 3

Figure 4:
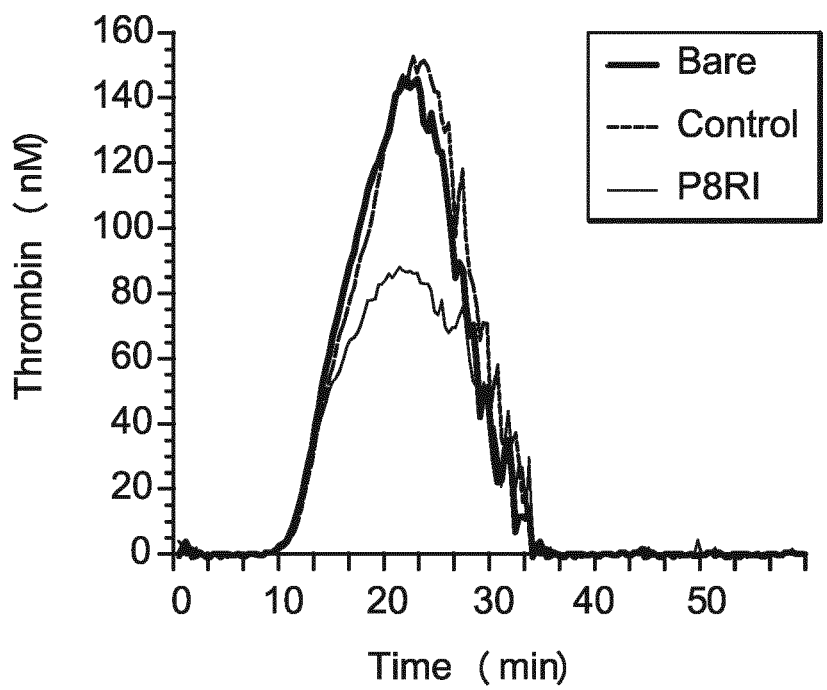
FIGS. 4-6 show that immobilised P8RI (SEQ ID NO:6) prevents platelet activation. Thrombin generation was measured at 37° C. by calibrated automated thrombogram in platelet rich plasma in the presence of Tissue Factor (0.5 pM) in aminated polystyrene wells. PERI was covalently bound onto the wells. A scramble peptide was used as negative control
Figure 5:
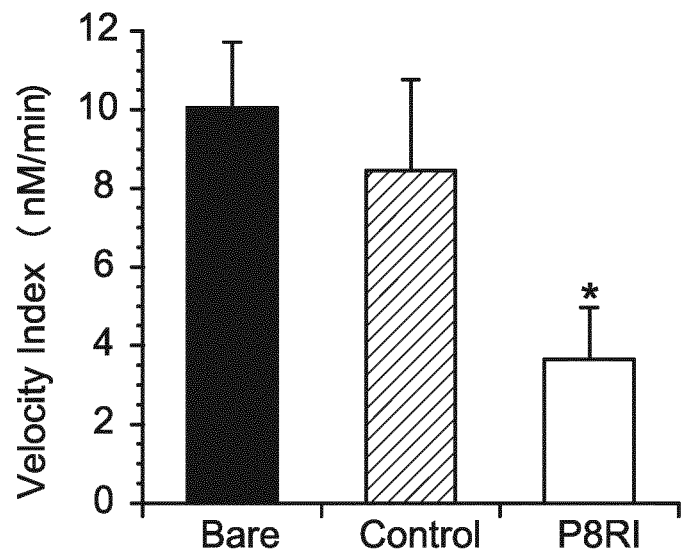
Figure 6:
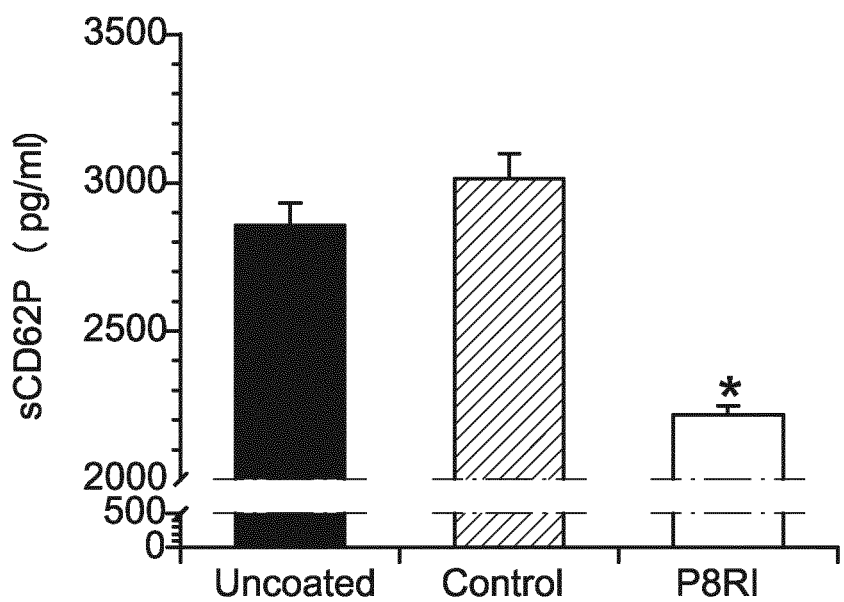

Effect of the Immobilised Peptide on Platelet Activation and Thrombin Generation Thrombin generation was measured at 37° C. by calibrated automated thrombogram (Hemker et al. Thromb Haemost. 2000; 83(4): 589-91) in platelet rich plasma (1.5× 10$^8$ platelets/nil) in the presence of Tissue Factor (0.5 pM) in aminated polystyrene wells (Covalink, Immunon® 2HB, Stago). SEQ ID NO 8 (P8RI, H-kwpalfvr-OH, MW 1016.26, TFA salt replaced by HCl salt, purity 100%, dissolved in water at 50 µM, pH 4-4.5) was pre-treated with EDC/S-NHS (10:1 molar ratio) and covalently bound onto the Immulon® wells. A scramble peptide was used as control peptide FIGS. 4-6 show that thrombin activity, calculated as Peak/Time to peak–LagTime, was significantly reduced in P8RI vs Bare and Control wells, and that the concentration of soluble P-selectin (sCD62P), released by platelets, was significantly reduced in the supernatant of P8RI-coated wells.

Example 4

Effect of the Soluble Peptide on Endothelial Cells

Figure 7:
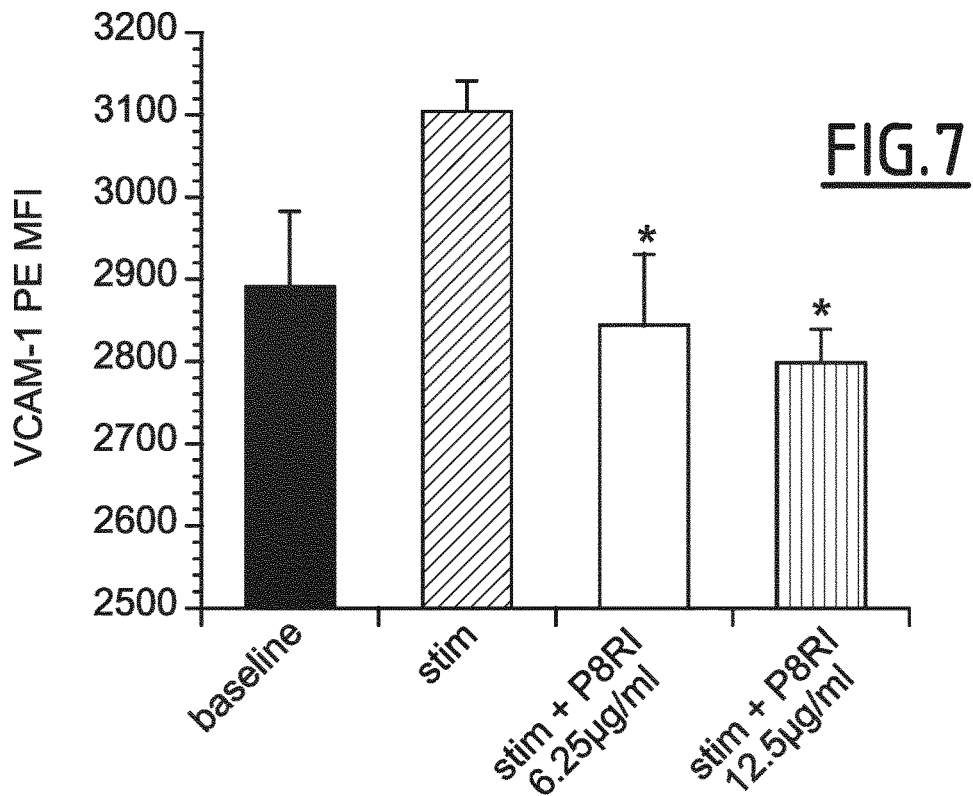
FIG. 7 shows the effect of the soluble peptides on VCAM-1 expression in D3 endothelial cells. The effect of P8RI (SEQ ID NO:6) on the expression of VCAM-1 was evaluated by quantitative FACS analysis on the immortalized human brain endothelial cell Line HCMEC/D3 submitted to overnight stimulation with TNFa (50 ng/ml) and IFNg (100 ng/ml).

The inventors evaluated the effect of P8RI on the expression of VCAM-1 by immunofluorescence on the immortalized human brain endothelial cell Line HCMEC/D3 submitted to overnight stimulation with TNFa (50 ng/ml) and IFNg (100 ng/ml). Although the increase in VCAM-1 expression was not impressive, the presence of the peptide prevented it (data not shown). Quantitative analysis by FACS of the same experimental conditions (FIG. 7) showed that the reduction of VCAM-1 expression observed in the "peptide" wells was statistically significant (n=3 wells/condition). The effect was observed already at 6.25 µg/ml and did not change with higher doses of the peptide (doses were up to 50 µg/ml).

P8RI (H-kwpalfvr-OH (SEQ ID NO 6) MW 1016.26, TFA salt replaced by HCl salt, purity 100%, dissolved in water at 50 µM, pH 4-4.5) was pre-treated with EDC/S-NHS (10:1 molar ratio) and covalently bound onto aminated polystyrene wells (Covalink, Immunon® 2HB, Stago). Control wells were coated with acetic acid (with EDC/S-NHS) as irrelevant source of COOH groups. Wells were blocked with endothelial cell culture medium supplemented with 3% FCS prior to seeding primary Human umbilical endothelial cells (HUVECs, 5×10$^5$ cells/ml). Three days later, P8RI-coated wells contained adherent and live cells (grey/translucent) while only dead cells/debris could be found in control wells (dark masses). This clearly demonstrated that immobilized P8RI favours endothelial cell attachment and growth onto solid supports.

Example 5

Curative Protocol in a Model of Multiple Sclerosis

Figure 8:
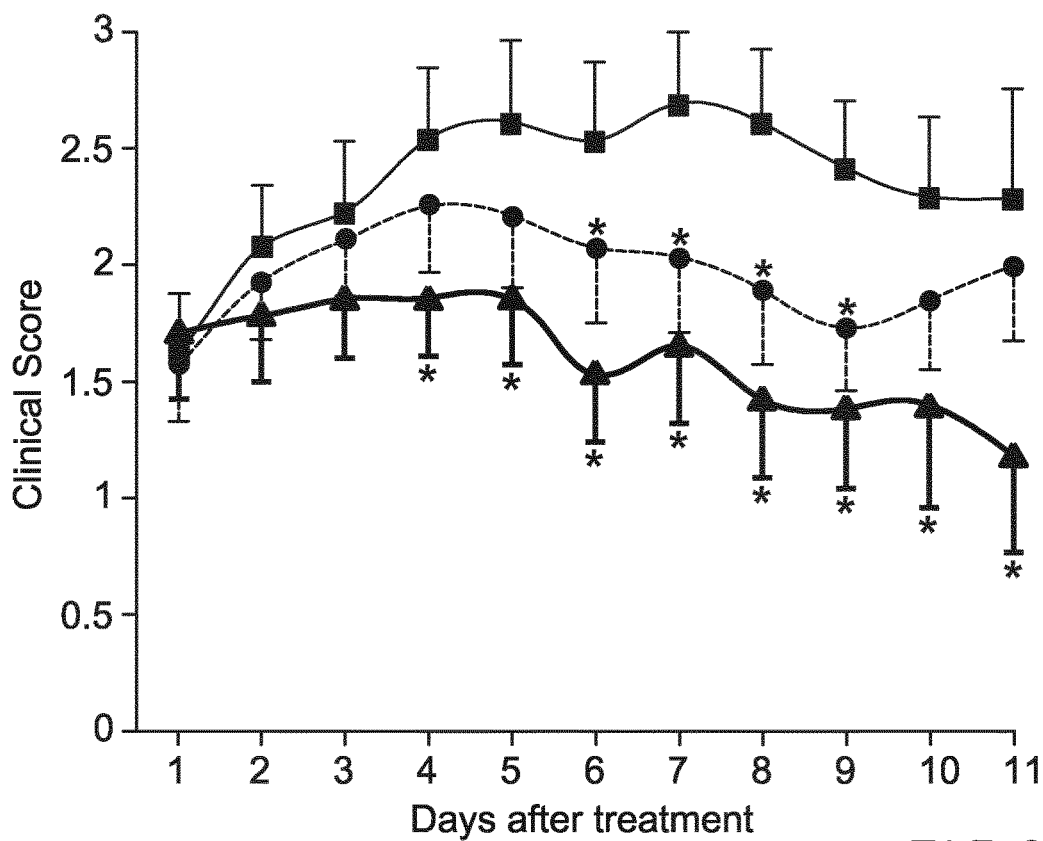
FIG. 8 demonstrates a therapeutic effect of P8RI peptide (SEQ ID NO:6) in experimental autoimmune encephalitis, a mouse model of multiple sclerosis. A curative assay was performed in the EAE mouse model by starting the administration of P8RI at 2 mg/kg/day subcutaneously after the onset of ascending paralysis (score.gtoreq.1), using prednisone as a pharmaceutical control. The figure shows ascending paralysis (clinical score) linked to active encephalitis in mice treated with vehicle (squares), prednisone at 2 mg/kg/day (circles) or P8RI at 2 mg/kg/day (triangles).

To demonstrate effectiveness of the peptides in an in vivo therapeutic protocol, a curative assay was performed in the EAE mouse model (experimental autoimmune encephalitis, a mouse model of multiple sclerosis), with prednisone used as a reference drug. P8RI was administered at 2 mg/kg/day, s.c. In the protocol used, the treatment started only once the clinical score was ≥1 (paralysis of the tail) and enrolled mice were followed up daily for 12 days. The reference drug (prednisone) was used at the same dosing schedule. As shown in FIG. 8, the CD31 peptide was even more rapid and effective than prednisone in reducing the extent of the ascending paralysis (clinical score) linked to active encephalitis in treated mice.

Example 6

Curative Protocol in a Model of Acute Thrombosis

Figure 9:
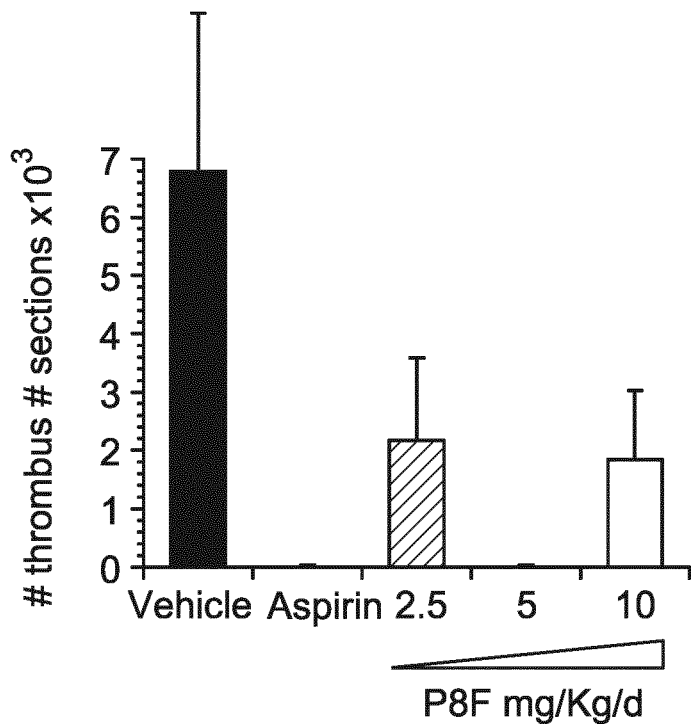
FIG. 9 demonstrates a therapeutic effect of P8F peptide (SEQ ID NO:5) in a mouse model of acture thrombosis. Atherosclerotic mice were treated with P8F at 2.5, 5 or 10 mg/kg/day, with aspirin as a positive control and vehicle as a negative control. The number of sections showing an occlusive thrombus, out of 1000 sections/sample, was significantly lowered in P8F-treated mice as compared to vehicle. No occlusive thrombus could be found in either the aspirin or the 5 mg/ml group
Figure 10:
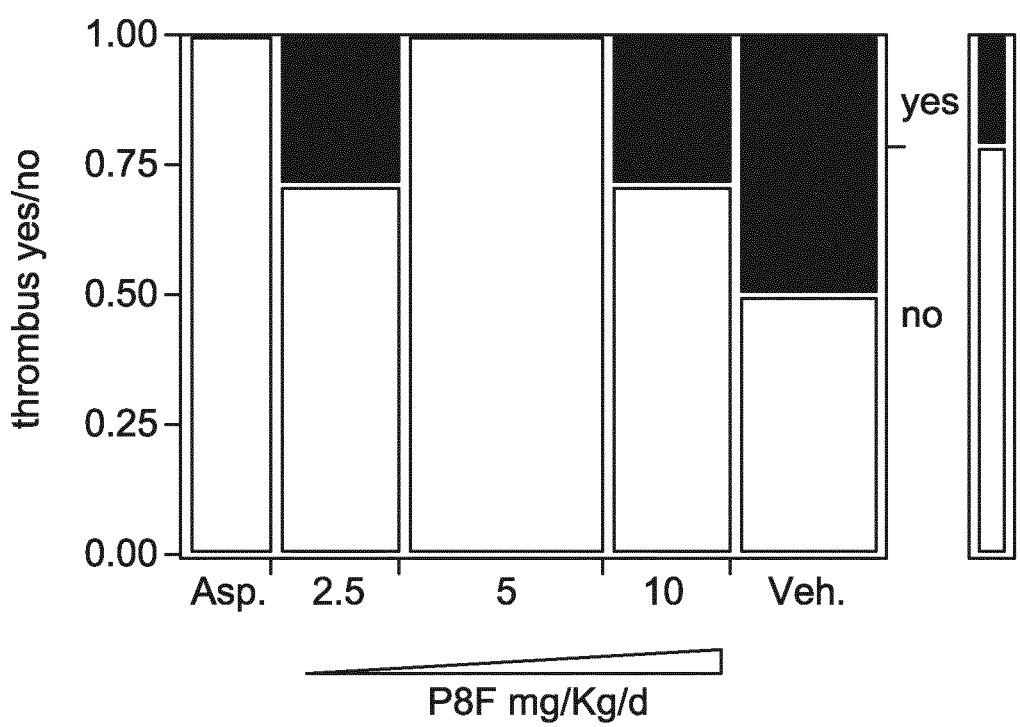
FIG. 10 shows a Cochran-Mantel-Haenszel test (Chi Square) analysis of the data presented in FIG. 9. The width of the columns is proportional to the number of mice included in each group (Aspirin=5, "2.5"=7, "5"=11, "10"=7, Vehicle=8). $P<0.05$ for all groups vs vehicle (Veh).

The P8F sequence was also used in vivo (subcutaneous administration of different doses: 2.5, 5 and 10 mg/kg/d) in atherosclerotic mice (apoE KO, 35 weeks of age, male, chow diet) subjected to the ligation of the left common carotid artery (a model of acute thrombosis). Due to advanced age, most of the mice had already developed an atherosclerotic lesion close to the site where the ligation was performed. Fluorescence photomicrography in cross sections stained with Evan's blue (fluorescent in the red channel) showed the occurrence of an occlusive thrombus over atherosclerotic lesions in untreated mice. The peptide was effective in preventing the appearance of an occlusive thrombus, at all the tested doses. The dose of 5 mg/Kg/d showed the same extent of antithrombotic effect as the reference drug (aspirin, given subcutaneously at 150 mg/kg/d). The number of sections showing an occlusive thrombus, out of 1000 sections/sample, was significantly lowered in P8F-treated mice as compared to vehicle (FIGS. 9 and 10). No occlusive thrombus could be found in either the aspirin or the 5 mg/ml group.

Example

7 Comparison of P8F and P8RI with Existing Peptides

The solubility, activity and stability (resistance to freezing/thawing) of the P8F and P8RI peptides were compared to previously used peptides comprising the membrane-proximal sequences of CD31.

The peptides used for the comparison were:
P8F
P8RI
P23 Hum—amino acids 579-601 of the human CD31 sequence of SEQ ID NO: 1
P22 mouse—amino acids 569-590 of the mouse CD31 sequence of SEQ ID NO: 2
PepReg—amino acids 581-590 of the mouse CD31 sequence of SEQ ID NO: 2.

Activity was determined using the calcium mobilization test using Jurkat T cells, as described above. The results are shown in Table 1 below and are expressed as ED 50 (the minimal dose producing 50 percent of the maximum obtainable inhibition of intracellular calcium mobilization in Jurkat cells stimulated with antiCD3+Fab antibodies).

Stability was determined by subjecting the peptides to repeated freeze-thaw cycles and determining the number of cycles after which ED 50 was increased and/or biological activity abolished. The activity of the peptides was diminished or abolished after the number of freeze-thaw cycles indicated in Table 1

As can be seen from table 1 below, P8F and P8RI were superior to the previously used peptides in all respects tested. They showed increased solubility, lower ED 50 and equal or improved stability. In addition, whereas the previously used peptides required organic solvent, P8F and P8RI were soluble in water, making them more suitable for medical applications.

TABLE I

|  | minimum purity (%) | minimal solvent | maximum soubility (mg/ml) | ED 50 ($\mu$M) | maximum freeze/thaw cycles |
|---|---|---|---|---|---|
| P8F | 99 | water | 28.1 | 25 | 3 |
| P8RI | 100 | water | 30.5 | 12.5 | 5 |
| P23 Hum | 97 | 10% Acetonitrile | 8.6 | 100 | 2 |
| P22 mouse | 96 | 10% Acetonitrile, 5% acetic acid | 15.9 | 100 | 2 |
| PepReg | 98 | 10% Acetonitrile, 5% acetic acid | 8.1 | 50 | 3 |

The invention claimed is:

1. A pharmaceutical composition comprising an isolated peptide consisting of:

|       |                  | (SEQ ID NO: 5) |
| ----- | ---------------- | -------------- |
| (i)   | H-RVFLAPWK-OH,   |                |
|       |                  | (SEQ ID NO: 6) |
| (ii)  | H-kwpalfvr-OH,   |                |
|       |                  | (SEQ ID NO: 7) |
| (iii) | H-RVILAPWK-OH,   |                |
|       |                  | (SEQ ID NO: 8) |
| (iv)  | H-kwpalivr-OH,   |                | or (v) a chemically modified peptide of (i), (ii), (iii), or (iv) which has at least one chemical modification selected from the group consisting of:

modification to the N-terminal and/or C-terminal end of the peptide by N-terminal acylation or deamination;

modification of the C-terminal carboxyl group into an amide or an alcohol group;

modification at the amide bond between two amino acids by acylation or alkylation at the nitrogen atom or the alpha carbon of the amide bond linking two amino acids;

modification at the alpha carbon of the amide bond linking two amino acids by acylation or alkylation at the alpha carbon of the amide bond linking two amino acids;

replacement of one or more alpha carbons with nitrogen atoms; and binding of the amino group of one or more amino acid to the β carbon rather than the α carbon.

2. The pharmaceutical composition according to claim 1, wherein said peptide is attached to a solid support.

3. The pharmaceutical composition according to claim 2, wherein said solid support is an intravascular prosthesis.

4. The pharmaceutical composition according to claim 3, wherein said intravascular prosthesis is a stent.

5. A medical device comprising an isolated peptide immobilized on a surface, wherein said peptide consists of:

|       |                  | (SEQ ID NO: 5) |
| ----- | ---------------- | -------------- |
| (i)   | H-RVFLAPWK-OH,   |                |
|       |                  | (SEQ ID NO: 6) |
| (ii)  | H-kwpalfvr-OH,   |                |
|       |                  | (SEQ ID NO: 7) |
| (iii) | H-RVILAPWK-OH,   |                |
|       |                  | (SEQ ID NO: 8) |
| (iv)  | H-kwpalivr-OH,   |                | or (v) a chemically modified peptide of (i), (ii), (iii), or (iv) which has at least one chemical modification selected from the group consisting of:

modification to the N-terminal and/or C-terminal end of the peptide by N-terminal acylation or deamination;

modification of the C-terminal carboxyl group into an amide or an alcohol group;

modification at the amide bond between two amino acids by acylation or alkylation at the nitrogen atom or the alpha carbon of the amide bond linking two amino acids;

modification at the alpha carbon of the amide bond linking two amino acids by acylation or alkylation at the alpha carbon of the amide bond linking two amino acids;

replacement of one or more alpha carbons with nitrogen atoms; and binding of the amino group of one or more amino acid to the β carbon rather than the α carbon.

6. The medical device according to claim 5, where said medical device is an intravascular prosthesis.

7. The medical device according to claim 6, wherein said intravascular prosthesis is a stent.

8. A method for activating CD31-mediated signaling in vivo in an individual in need thereof, wherein said method comprises a step of administering to said individual a peptide consisting of:

|       |                  | (SEQ ID NO: 5) |
| ----- | ---------------- | -------------- |
| (i)   | H-RVFLAPWK-OH,   |                |
|       |                  | (SEQ ID NO: 6) |
| (ii)  | H-kwpalfvr-OH,   |                |
|       |                  | (SEQ ID NO: 7) |
| (iii) | H-RVILAPWK-OH,   |                |
|       |                  | (SEQ ID NO: 8) |
| (iv)  | H-kwpalivr-OH,   |                | or (v) a chemically modified peptide of (i), (ii), (iii), or (iv) which has at least one chemical modification selected from the group consisting of:

modification to the N-terminal and/or C-terminal end of the peptide by N-terminal acylation or deamination;

modification of the C-terminal carboxyl group into an amide or an alcohol group;

modification at the amide bond between two amino acids by acylation or alkylation at the nitrogen atom or the alpha carbon of the amide bond linking two amino acids;

modification at the alpha carbon of the amide bond linking two amino acids by acylation or alkylation at the alpha carbon of the amide bond linking two amino acids;

replacement of one or more alpha carbons with nitrogen atoms; and binding of the amino group of one or more amino acid to the β carbon rather than the α carbon.

9. The method according to claim 8, wherein said peptide is attached to a solid support.

10. The method according to claim 8, wherein the peptide is administered subcutaneously.

11. The method according to claim 9, wherein said solid support is an intravascular prosthesis.

12. A method for the treatment of atherosclerosis or multiple sclerosis in an individual in need thereof, wherein said method comprises a step of administering to said individual a peptide consisting of:

(i) H-RVFLAPWK-OH, (SEQ ID NO: 5)

(ii) H-kwpalfvr-OH, (SEQ ID NO: 6)

(iii) H-RVILAPWK-OH, (SEQ ID NO: 7)

(iv) H-kwpalivr-OH, (SEQ ID NO: 8)

or (v) a chemically modified peptide of (i), (ii), (iii), or (iv) which has at least one chemical modification selected from the group consisting of:

modification to the N-terminal and/or C-terminal end of the peptide by N-terminal acylation or deamination;

modification of the C-terminal carboxyl group into an amide or an alcohol group;

modification at the amide bond between two amino acids by acylation or alkylation at the nitrogen atom or the alpha carbon of the amide bond linking two amino acids;

modification at the alpha carbon of the amide bond linking two amino acids by acylation or alkylation at the alpha carbon of the amide bond linking two amino acids;

replacement of one or more alpha carbons with nitrogen atoms; and binding of the amino group of one or more amino acid to the β carbon rather than the α carbon.

13. The method according to claim 12, wherein the peptide is attached to a solid support.

14. The method according to claim 13, wherein said solid support is an intravascular prosthesis.

15. The method according to claim 12, wherein the peptide is administered subcutaneously.

* * * * *